(12) United States Patent
Stuhlmann et al.

(10) Patent No.: US 11,801,210 B2
(45) Date of Patent: Oct. 31, 2023

(54) RETINOL REPLACEMENT IN SKIN TREATMENT

(71) Applicant: SYMRISE AG, Holzminden (DE)

(72) Inventors: Dominik Stuhlmann, Holzminden (DE); Ann-Christin Weseloh, Polle (DE); Nicole Titze, Holzminden (DE); Sabine Lange, Holzminden (DE); Sebastian Bruncke, Höxter (DE); Benoît Join, Holzminden (DE); Gabriele Vielhaber, Colombes (FR); Marielle Le Maire, Boulogne (FR); Karima Benaissi, Saint-Ouen (FR)

(73) Assignee: SYMRISE AG, Holzminden (DE)

( * ) Notice: Subject to any disclaimer, the term of this patent is extended or adjusted under 35 U.S.C. 154(b) by 109 days.

(21) Appl. No.: 17/042,263

(22) PCT Filed: Mar. 29, 2019

(86) PCT No.: PCT/EP2019/058097
§ 371 (c)(1),
(2) Date: Sep. 28, 2020

(87) PCT Pub. No.: WO2019/185923
PCT Pub. Date: Oct. 3, 2019

(65) Prior Publication Data
US 2021/0045983 A1 Feb. 18, 2021

(30) Foreign Application Priority Data
Mar. 29, 2018 (WO) ................ PCT/EP2018/058113

(51) Int. Cl.
| | | |
|---|---|---|
| *A61K 8/37* | (2006.01) |
| *A61P 17/02* | (2006.01) |
| *A61K 31/01* | (2006.01) |
| *A61K 31/047* | (2006.01) |
| *A61K 31/198* | (2006.01) |
| *A61K 31/22* | (2006.01) |
| *A61K 31/225* | (2006.01) |
| *A61K 31/23* | (2006.01) |
| *A61K 31/232* | (2006.01) |
| *A61K 31/355* | (2006.01) |
| *A61K 31/357* | (2006.01) |
| *A61K 36/28* | (2006.01) |
| *A61K 36/886* | (2006.01) |
| *A61K 36/9068* | (2006.01) |
| *A61Q 17/04* | (2006.01) |
| *A61Q 19/00* | (2006.01) |
| *A61Q 19/08* | (2006.01) |

(52) U.S. Cl.
CPC ............... *A61K 8/37* (2013.01); *A61K 31/01* (2013.01); *A61K 31/047* (2013.01); *A61K 31/198* (2013.01); *A61K 31/22* (2013.01); *A61K 31/225* (2013.01); *A61K 31/23* (2013.01); *A61K 31/232* (2013.01); *A61K 31/355* (2013.01); *A61K 31/357* (2013.01); *A61K 36/28* (2013.01); *A61K 36/886* (2013.01); *A61K 36/9068* (2013.01); *A61P 17/02* (2018.01); *A61Q 17/04* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,885,311 A | 12/1989 | Parish et al. | |
| 5,578,641 A * | 11/1996 | Jackson | ................... A61K 8/68 |
| | | | 514/847 |
| 2007/0166267 A1 | 7/2007 | Majewski et al. | |
| 2008/0139518 A1 | 6/2008 | Purcell | |

FOREIGN PATENT DOCUMENTS

| | | |
|---|---|---|
| CN | 106852126 A | 6/2017 |
| WO | 88/09788 A1 | 12/1988 |
| WO | 8809788 A1 | 12/1988 |
| WO | 90/06751 A1 | 6/1990 |
| WO | 9006751 A1 | 6/1990 |
| WO | WO-2006/053006 A2 * | 5/2006 |
| WO | 2008/070116 A2 | 6/2008 |
| WO | 2012/051614 A2 | 4/2012 |
| WO | 2012051614 A2 | 4/2012 |
| WO | 2015/187921 A1 | 12/2015 |

OTHER PUBLICATIONS

Kollmer et al., Investigation of the Compatibility of the Skin PAMPA Model with Topical Formulation and Acceptor Media Additives Using Different Assay Setups, 2019, AAPS PharmSciTech, 20: 89.*
Ruth et al., Antiaging effects of retinoid hydroxypinacolone retinoate on skin models, Sep. 2018, J Am Acad Dermatol, AB44, 7932.*
International Search Report and Written Opinion dated May 24, 2019 for corresponding PCT Application No. PCT/EP2019/058097.
European Office Action dated Sep. 24, 2021 for corresponding European Application No. 19714432.2.
Paul A. Lehman et al., "Percutaneous Absorption of Retinoids: Influence of Vehicle, Legit Exposure, and Dose," The Journal of Investigative Dermatology, vol. 91, No. 1, 1988; pp. 56-61 XP055005374.

(Continued)

*Primary Examiner* — Terry A Mckelvey
*Assistant Examiner* — Catheryne Chen
(74) *Attorney, Agent, or Firm* — POLSINELLI PC

(57) ABSTRACT

The present invention relates to novel cosmetic and therapeutic uses of one or more compounds of the general formula (1) as described herein. Furthermore, the present invention relates to compositions (products or, respectively, formulations), in particular for topical administration, preferably cosmetic or pharmaceutical compositions, comprising or consisting of compound(s) of formula (1) and one or more cosmetically and/or pharmaceutically acceptable carriers. The present invention also relates to novel uses of such compositions according to the invention.

15 Claims, 3 Drawing Sheets

(56) References Cited

OTHER PUBLICATIONS

Chinese Office Action dated Aug. 29, 2022 for corresponding Chinese Application No. 201980023365.7.

* cited by examiner

RETINOL REPLACEMENT IN SKIN TREATMENT

CROSS-REFERENCE TO RELATED APPLICATIONS

This application is a national stage application (under 35 U.S.C. § 371) of PCT/EP2019/058097, filed Mar. 29, 2019, which claims benefit of PCT Application No. PCT/EP2018/058113, filed Mar. 29, 2018, which are incorporated herein by reference in their entireties.

FIELD OF THE DISCLOSURE

The present invention primarily relates to novel cosmetic and therapeutic uses of a mixture comprising or consisting of one or more compounds of the general formula 1

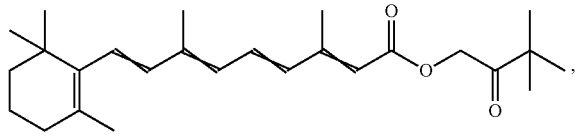

(formula 1)

and diisopropyl adipate.

BACKGROUND OF THE DISCLOSURE

Retinol and its derivatives (retinoic acid, retinoyl-pamitate, retinoyl-acetate) are widely used in the cosmetics industry as anti-aging compounds and to a lesser extend as anti-oily skin actives. Compositions comprising retinol and its derivatives and methods for the uses thereof are e.g. described in WO 2016/118281 A1, US 2013/0310355 A1 or WO 2014/116653 A1.

However, problematically, after longer exposure with compositions of prior art, skin often reacts with inflammation, allergic reaction, redness, peeling, dryness, itch or UV protection weakness.

WO 2012/051614 A2 describes a composition for topical delivery of a bioactive agent to a subject, wherein the agent can be a Vitamin A derivative, in particular a retinoid.

SUMMARY OF THE DISCLOSURE

Furthermore, the present invention relates to compositions (products or, respectively, formulations), in particular for topical administration, preferably cosmetic or pharmaceutical compositions, comprising or consisting of such a mixture and optionally one or more cosmetically and/or pharmaceutically acceptable carriers.

The present invention also relates to novel uses of such a mixture according to the invention.

Further aspects of the present invention become apparent by studying the following specification, the examples described herein as well as the attached claims.

In particular, in the cosmetics and pharmaceuticals industry, there is a constant need for agents for improving the complexion of human skin. Furthermore, there is a constant need for agents suitable for use in the treatment and/or prevention of diseases associated with/caused by unhealthy conditions of the human skin. The skin, in particular the epidermis, as a barrier organ of the human organism is subjected to external influences to a particular extent. Many intrinsic factors (e.g. genetic predisposition) and extrinsic factors (e.g. damage to the skin barrier) can lead to anaesthetic or painful symptoms.

BRIEF DESCRIPTION OF THE DRAWINGS

Implementation of the present technology will now be described, by way of example only, with reference to the attached figures, wherein.

Figure 1:
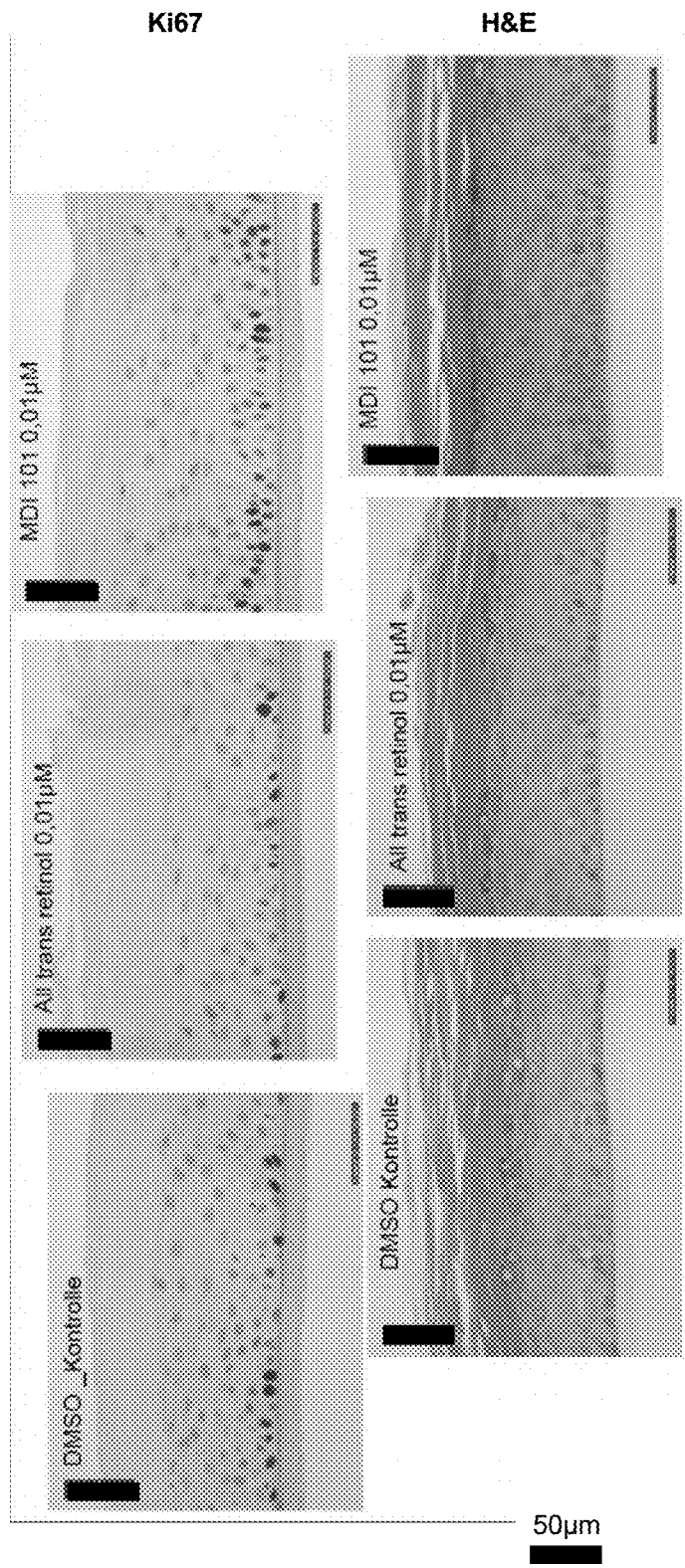
FIG. 1 shows images showing the MDI 101, all-trans Retinol, the DMSO (control), all in a concentration of 0.01 µM across the thickness of thickness of the epidermis according to aspects of the disclosure.
Figure 2:
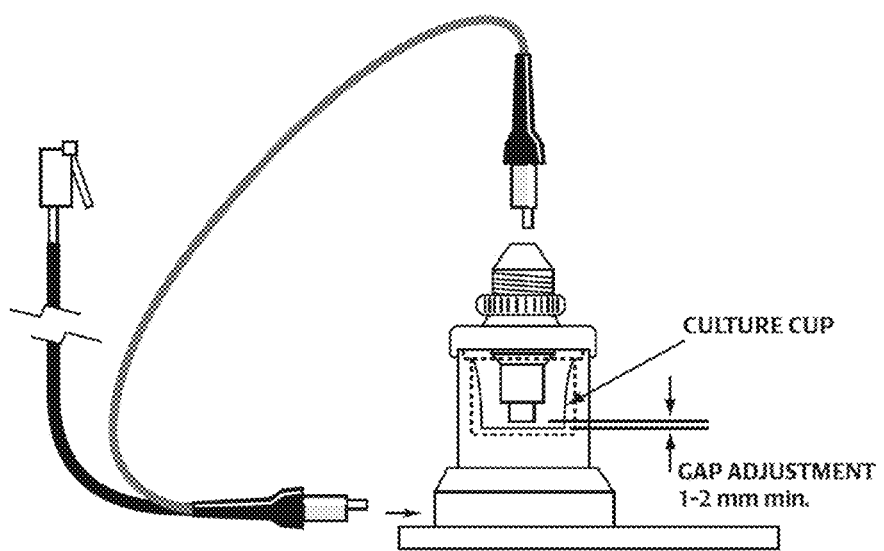
FIG. 2 is a schematic of a system for assessing cells in a culture cup in accordance with aspects of the disclosure.

It should be understood that the various aspects are not limited to the arrangements and instrumentality shown in the drawings.

DETAILED DESCRIPTION OF THE DISCLOSURE

The inventors of the present invention tried to find a retinol replacer that copies the positive effects of retinol without the negative side effects that come from longer exposure. A particular focus was on the skin barrier improvement capacity, that seems responsible for the positive effects like anti-inflammatory response, epidermal cell growth and differentiation, increase of collagen production, improvement of sebaceous glands function, reversal of photo-aging phenomenon, inhibition of melanin production, promotion of skin thickening, etc.

However, many suitable substances are difficult to dissolve or to maintain in a dissolved condition. Such substances easily precipitate and crystallize. In such a condition, their effect is drastically reduced or not present at all.

Primary object of the present invention was thus to provide suitable agents in a dissolved condition, having, preferably improved, actions as described above, and, preferably, being toxicologically acceptable, tolerated well by the skin and being stable in conventional cosmetic and/or pharmaceutical formulations, having the lowest possible intrinsic odour and the lowest possible intrinsic colour, and preferably being inexpensive to prepare. Furthermore, preferably agents with retinol like activities at lower concentration should be provided.

Further objects of the present invention can be derived from the following specification, the examples described herein as well as, in particular, the attached claims.

The primary object of the present invention is achieved by a cosmetic, non-therapeutic use of a mixture comprising or consisting of a) one or more compound(s) of formula 1

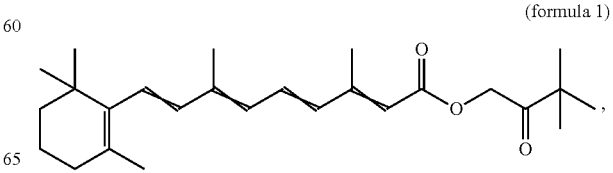

(formula 1)

and b) diisopropyl adipate, for non-therapeutically improving the complexion of human skin, preferably for non-therapeutically improving the complexion of human facial skin, and/or as non-therapeutic anti-aging compound.

In formula 1, the crossed lines designate double bonds and mean, independently from each other, an (E) or (Z) configuration. Preferably, one, more or all crossed lines mean an (E) configuration.

Hydroxypinacolone Retinoate (MDI 101) is a powder with poor solubility in e.g. cosmetic or pharmaceutical compositions (e.g. emulsions).

Incorporating the sole powder in such compositions leads to recrystallization of MDI 101 in the composition. This is a big disadvantage for e.g. cosmetic and pharmaceutical compositions as it has a negative impact on physical product stability. Furthermore, it leads to reduced bioavailability & efficacy of the MDI 101 since it is thus not properly dissolved.

Figure 3:
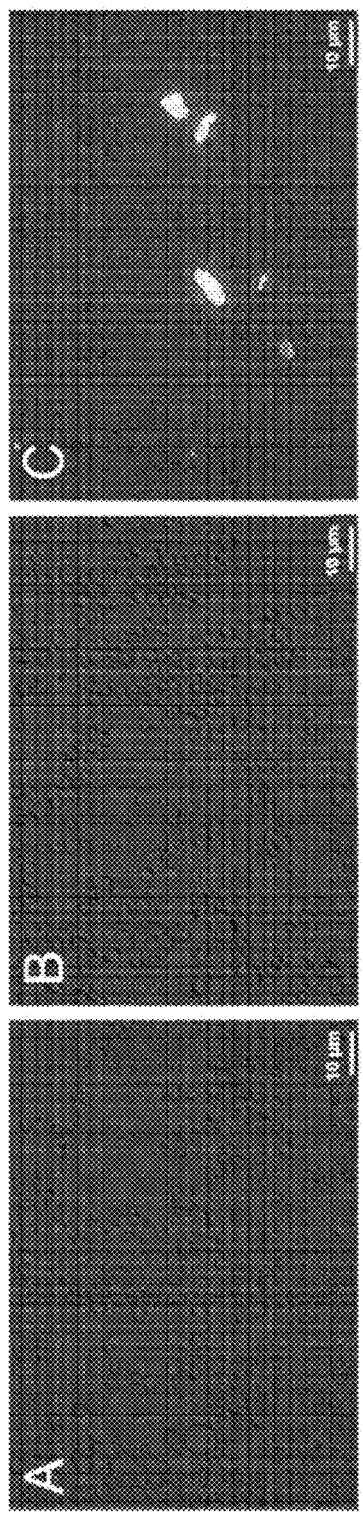
FIG. 3 shows microscopic images of exemplary emulsion compositions according to aspects of the disclosure.

It was surprisingly found that pre-solving Hydroxypinacolone Retinoate (MDI 101) in diisopropyl adipate strongly improved the solubility and a recrystallization could be avoided (see example 1.6 and FIG. 3).

The primary object of the invention is also achieved by a mixture comprising or consisting of one or more compound(s) of formula 1 (as shown above) and diisopropyl adipate for use in the treatment or prevention of one or more diseases or unhealthy conditions of human skin, preferably of human facial skin.

Preferably, the mixture according to the invention is used
(i) for thickening the epidermis, preferably via its pro-proliferative activity, and/or
(ii) for increasing the number of living skin layers, and/or
(iii) for improving the skin barrier, and/or
(iv) for improving the organization of the stratum corneum, and/or
(v) for decreasing the skin tissue's irritant potential, and/or
(vi) as anti-oxidative agent(s), and/or
(vii) for treating or preventing one or more skin diseases in aging.

Formula 1 denotes retinoic acid, 3,3-dimethyl-2-oxobutyl ester (CAS 893412-73-2; MDI 101) and its isomers. The main structure is:

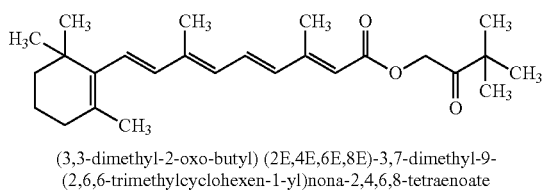 [SMILES: CC1=C(/C=C/C(C)=C/C=C/C(C)=C/C(=O)OCC(=O)C(C)(C)C)C(C)(C)CCC1]

(3,3-dimethyl-2-oxo-butyl) (2E,4E,6E,8E)-3,7-dimethyl-9-(2,6,6-trimethylcyclohexen-1-yl)nona-2,4,6,8-tetraenoate The stability of this structure in darkness is >99%. In light, further isomers arise. These isomers are just as active as the main structure and are present in a fluctuating proportion of 0 to 30%. Such Isomers are for example the following structures:

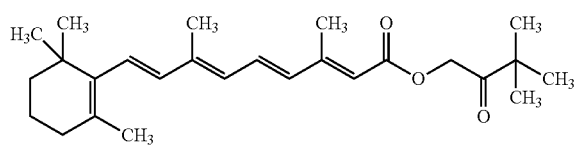

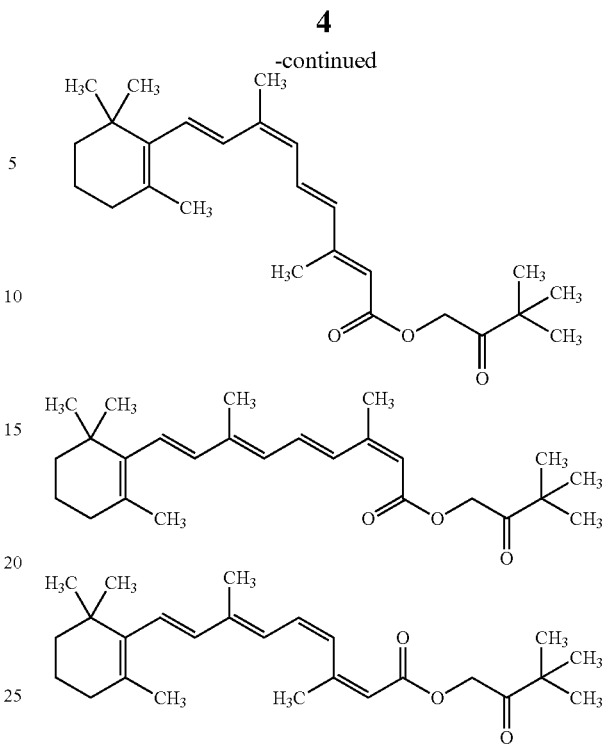

For retinoic acid, 3,3-dimethyl-2-oxobutyl ester, further isomers are possible. Formula 1 as well as the main structure are meant to be understood as representative for all possible isomers, i.e. as described above, the crossed lines designate double bonds and mean, independently from each other, an (E) or (Z) configuration. The term "one or more compounds" is meant to be understood as one or more different isomers represented by general formula I. Thus, the term "one or more compounds" also includes a mixture of two or more different isomers.

The compounds described herein are particularly able to thicken the epidermis by their pro-proliferative activity, leading to an increased number of living skin layers. Additionally, the organization of the stratum corneum is improved.

Additionally, the tox-profile of the compounds described herein is superior.

Furthermore, advantageously the compounds described herein have no or only low intrinsic colour.

It is preferred that the mixture according to the invention comprises or consists of 0.5 to 10 wt.-%, preferably 1 to 5 wt.-%, particularly preferably 2 to 3 wt.-% of MDI 101 and diisopropyl adipate. Preferably, the mixture according to the invention further comprises 0.1 to 5 wt.-%, preferably 0.25 to 2 wt.-%, particularly preferably 0.5 to 1.5 wt.-% of tocopherol.

It is particularly preferred that the mixture according to the invention consists of 0.5 to 10 wt.-%, preferably 1 to 5 wt.-%, particularly preferably 2 to 3 wt.-% of MDI 101, 0.1 to 5 wt.-%, preferably 0.25 to 2 wt.-%, particularly preferably 0.5 to 1.5 wt.-% of tocopherol and the diisopropyl adipate content is added up to 100 wt.-%.

According to a preferred aspect, the mixture according to the invention is used in a cosmetic composition, wherein the total amount of compound(s) of formula 1 in the composition is in the range of from 0.0001 to 1.0 wt.-%, preferably from 0.001 to 0.2 wt.-%, particularly preferably from 0.001 to 0.1 wt.-%.

According to another preferred aspect, the mixture for use as described herein is used in a pharmaceutical composition, wherein the total amount of compound(s) of formula 1 in the composition is in the range of from 0.0001 to 1.0 wt.-%, preferably from 0.001 to 0.2 wt.-%, particularly preferably from 0.001 to 0.1 wt.-%.

Preferably, the mixture is used in combination with one or more (further) substances for preventing, reducing or alleviating itchy skin condition(s) and/or one or more skin irritation-reducing agents, in particular one or more substances selected from the group consisting of anti-inflammatory agents, physiological cooling agents and compounds that alleviate reddening, preferably wherein the one or more additional substances is/are selected from the group consisting of:

(i) anti-itch compounds,
(ii) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone,
(iii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone,
(iv) natural or naturally occurring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof,
(v) alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, glabridin and licochalcone A, preferably in the form of pure substances,
(vi) skin care agents, preferably skin moisture retention regulators or skin repair agents, preferably selected from the group consisting of sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-)ceramides (preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide), glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy fatty acids, triterpenic acids, such as betulic acid or ursolic acid, and algae extracts or single active compounds thereof,
(vii) physiological cooling agents, preferably selected from the group consisting of menthone glycerol acetal, menthyl lactate preferably l-menthyl lactate, in particular l-menthyl l-lactate), menthyl ethyl oxamate, substituted menthyl-3-carboxylic acid amides (e.g. menthyl-3-carboxylic acid N-ethylamide, $N^{\alpha}$-(L-menthanecarbonyl)glycine ethyl ester, 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin, and
(viii) histamine receptor antagonists, serine protease inhibitors, TRPV1 antagonists, NK1 antagonists, cannabinoid receptor agonists and TRPV3 antagonists.

Preferably, the mixture is used in combination with vitamin E and/or derivatives (preferably tocopherol, tocopheryl acetate) as skin care agents. It is further preferred if in this case, the compound(s) of formula 1 are present in the range of from 0.001 to 0.1 wt.-%, based on the total composition it is used in.

Further substances and, respectively, classes of substances, for example auxiliary substances and additives, that may be used in combination with the mixture described herein will be described below.

Due to the effect of diisopropyl adipate, the compounds of formula 1 described herein, i.e. as a mixture as described herein, are particularly suitable to be incorporated in cosmetic and pharmaceutical compositions. Thus, a further aspect of the present invention relates to corresponding compositions. A composition according to the present invention is preferably for topical administration and preferably a cosmetic or pharmaceutical composition, and comprises or consists of a) the mixture as defined in claim 1,
   wherein the compound(s) of formula 1 are in the range of from 0.0001 to 2 wt.-%, range of from 0.0001 to 1.0 wt.-%, preferably from 0.001 to 0.2 wt.-%, particularly preferably from 0.001 to 0.1 wt.-%. preferably from 0.001 to 0.1 wt.-% related to the total amount of the composition,
   and
b) optionally: one or more cosmetically and/or pharmaceutically acceptable carriers.

According to a preferred embodiment, the cosmetically and/or pharmaceutically acceptable carriers are carriers other than water, more preferably carriers selected from the group consisting of glycols, aliphatic esters, in particular aliphatic esters showing good solubilising properties for one, more or all of the substances of component a), preferably polyethyleneglycol esters and polyethyleneglycol ethers or mixtures thereof, in particular cosmetically and/or pharmaceutically acceptable carriers for enhancing the bioavailability of one, more or all of the substances of component a).

Also preferred is the use of one or more carriers selected from
- one or more diols, preferably alkane diol(s), having 3 to 10 carbon atoms, preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methyl-pentane-2,4-diol, 1,2-hexanediol, 1,6-hexanediol, 1,2-octanediol, 1,2-decanediol and/or
- cosmetically acceptable carriers selected from groups (i) and/or (ii) and/or (iii) and/or (iv) or mixtures thereof, said groups consisting of (i) aliphatic esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl isononanoate, palmityl isononanoate, cetearyl isononanoate, palmityl 3,5,5-trimethylhexanoate, stearyl 3,5,5-trimethylhexanoate, cetearyl 3,5,5-trimethylhexanoate, stearyl heptanoate, stearyl caprylate, 2-octydodecyl palmitate, oleyl oleate, oleyl erucate, erucyl oleate, erucyl erucate, 2-ethylhexyl isostearate, isotridecyl isononanoate, 2-ethylhexyl cocoate, C12-15-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or (ii) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or (iii) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methylphenyl siloxane, (iv) miscellaneous other solvents like acetone, methylpropyl ketone, dipropyl ketone, dimethyl sulfoxide, glycerine carbonate, propylene carbonate, butylene carbonate, glycerine formal, solketal, 2-ethyl hexanol, 2-butyl octanol, 2-hexyl decanol or 2-octyl dodecanol.

Compositions comprising one or more cosmetically acceptable carriers as described above are easy to handle and stable over a long period of time.

Compositions according to the present invention preferably comprise a total amount of 50 wt. % or more, more preferably at least 70 wt. %, even more preferably 80 wt. % to 90 wt. % or more, most preferably in a total amount of at least 95 wt. % or more and most preferred in a total amount of 95 to 99 wt. %, of carrier(s), preferably of the one or more (preferred) carriers as described above, in each case based on the total weight of the composition.

In any way, it is particularly preferred that the total amount of compound(s) of formula 1 in the mixture is sufficient to show one, more or all of the herein described activities when the mixture or a composition comprising such mixture is applied to a subject or respectively, a subject's skin, preferably a subject's facial skin.

The dosage regimen will be determined by e.g. the attending physician and other clinical factors. As is well known in the arts, dosages for any one subject depends upon many factors, including the patient's size, body surface area, age, sex, time and route of administration, general health, and other drugs being administered concurrently. Progress can be monitored by periodic assessment.

Preferably, as mentioned above in connection with the uses according to the present invention, such a composition additionally comprises one or more (further) substances for preventing, reducing or alleviating itchy skin condition(s) and/or one or more skin irritation-reducing agents, in particular one or more substances selected from the group consisting of anti-inflammatory agents, physiological cooling agents and compounds that alleviate reddening, preferably wherein the one or more additional substances is/are selected from the group consisting of:

(i) anti-itch compounds, (ii) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone, (iii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone, (iv) natural or naturally occurring anti-inflammatory substances or substances that alleviate reddening and/or itching, in particular extracts or fractions from camomile, Aloe vera, *Commiphora* species, *Rubia* species, willow, willow-herb, oats, calendula, arnica, St John's wort, honeysuckle, rosemary, *Passiflora incarnata*, witch hazel, ginger or *Echinacea*, or single active compounds thereof, (v) alpha-bisabolol, apigenin, apigenin-7-glucoside, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, glabridin and licochalcone A, preferably in the form of pure substances, (vi) skin care agents, preferably skin moisture retention regulators or skin repair agents, preferably selected from the group consisting of sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-)ceramides (preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide), glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts or single active compounds thereof, (vii) physiological cooling agents, preferably selected from the group consisting of menthone glycerol acetal, menthyl lactate preferably I-menthyl lactate, in particular I-menthyl I-lactate), menthyl ethyl oxamate, substituted menthyl-3-carboxylic acid amides (e.g. menthyl-3-carboxylic acid N-ethylamide, N$^\alpha$-(L-menthanecarbonyl)glycine ethyl ester, 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-on-ecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin, and (viii) histamine receptor antagonists, serine protease inhibitors, TRPV1 antagonists, NK1 antagonists, cannabinoid receptor agonists and TRPV3 antagonists.

Preferably, a composition according to the present invention is selected from the group of pharmaceutical and/or cosmetic products for treatment, protecting, care and cleansing of the skin and/or hair or as a make-up product, preferably as a leave-on product, more preferably in the form or selected from the product group consisting of alcoholic or aqueous/alcoholic solution, dispersion, suspension, emulsion (preferably cream, lotion or milk of the W/O, O/W or multiple emulsion, PIT emulsion, emulsion foam, micro-, nanoemulsion, Pickering emulsion type), ointment, paste, gel (preferably hydro-, hydrodispersion-, oleogel), balm, serum, powder, wipe, Eau de Toilette, Eau de Cologne, perfume, stick, roll-on, (pump) spray, aerosol, leave-on skin care composition (preferably face-care composition), leave-on insect repellent composition, sunscreen composition, skin-lightening composition, self-tanning composition, aftersun preparation, shaving or after-shave composition, hair-removing composition, hair care composition, preferably conditioner, hair lotion, hair tonic, styling cream, pomade, styling aid (preferably gel or wax), permanent wave and fixing compositions, hair smoothing composition (straightening composition, relaxer), hair setting composition, blonding composition, hair colouring composition, such as e.g. temporary, directly absorbed, semi-permanent hair colouring composition, permanent hair colouring composition, decorative cosmetic composition (preferably face powder, eye shadow, kajal pencil, lipstick), deodorant and/or antiperspirant composition.

It is particularly preferred that the composition is a cosmetic composition and the compound(s) of formula 1 are present in the composition in a range of from 0.001 to 0.2 wt.-%, particularly preferably from 0.001 to 0.1 wt.-%, based on the composition. It is additionally preferred that the composition further comprises vitamin E and/or derivatives (preferably tocopherol, tocopheryl acetate) as skin care agents, if not already present in the mixture according to the invention. Such a cosmetic composition, i.e. preferably comprising vitamin E and/or derivatives as described and with the compound(s) of formula 1 in an amount as described, can advantageously be used for non-therapeutically improving the complexion of human skin, preferably for non-therapeutically improving the complexion of human facial skin, and/or as non-therapeutic anti-aging compound. The invention thus also encompasses such a cosmetic composition for such use.

It is particularly preferred that the composition is a pharmaceutical composition and the compound(s) of formula 1 are present in the composition in a range of from 0.001 to 0.2 wt.-%, particularly preferably from 0.001 to 0.1 wt.-%, based on the composition. It is additionally preferred that the composition further comprises vitamin E and/or derivatives (preferably tocopherol, tocopheryl acetate) as skin care agents, if not already present in the mixture according to the invention. Such a pharmaceutical composition, i.e. preferably comprising vitamin E and/or derivatives as described and with the compound(s) of formula 1 in an amount as described, can advantageously be used for treatment of prevention of one or more diseases or unhealthy conditions of human skin, preferably of human facial skin. The invention thus also encompasses such a cosmetic composition for such use.

It is apparent that the cosmetic compositions of the present invention are also suitable for the cosmetic, non-therapeutic use for non-therapeutically improving the complexion of human skin, preferably for non-therapeutically improving the complexion of human facial skin, and/or as non-therapeutic anti-aging composition.

Similarly, the pharmaceutical compositions of the present invention are also suitable for use in the treatment or prevention of one or more diseases or unhealthy conditions of human skin, preferably of human facial skin. More preferably, such a composition is used (i) for thickening the epidermis, preferably via its proliferative activity, and/or
(ii) for increasing the number of living skin layers, and/or
(iii) for improving the skin barrier, and/or
(iv) for improving the organization of the stratum corneum, and/or
(v) for decreasing the skin tissue's irritant potential, and/or
(vi) as anti-oxidative agent(s), and/or
(vii) for treating or preventing one or more skin diseases in aging.

In connection with the present invention, it is preferred that the composition according to the present invention is used such that it remains for at least 5 minutes, preferably for at least 10 minutes, on the subject's (human's) skin ("leave-on product").

The pharmaceutical compositions described herein can be employed in the field of human medicine against a large number of topical (e.g. itchy) conditions and diseases of the skin.

Of course, the above explanations regarding preferred compounds to be used in connection with the present invention or preferred effects/uses thereof also apply to a composition according to the present invention.

In a preferred embodiment, a composition according to the present invention additionally comprises one or more fragrance materials. Suitable fragrance materials are mentioned in S. Arctander, Perfume and Flavor Chemicals, Vol. I and II, Montclair, N. J., 1969, self-published or H. Surburg and J. Panten, Common Fragrance and Flavor Materials, 5th. Ed., Wiley-VCH, Weinheim 2006, particularly those explicitly mentioned in US 2008/0070825.

Compositions according to the present invention advantageously comprise a total amount of 0.1 to 5 wt. %, preferably 0.2 to 4 wt. %, more preferably 0.25 to 3 wt. %, even more preferably 0.3-2.5 wt. %, of the one or more (preferred) fragrance materials, in each case based on the total weight of the composition or product.

A composition according to the present invention can be (further) processed by encapsulation with a solid shell material, which is preferably chosen from starches, degraded or chemically or physically modified starches (in particular dextrins and maltodextrins), gelatines, wax materials, liposomes, gum arabic, agar-agar, ghatti gum, gellan gum, modified and non-modified celluloses, pullulan, curdlan, carrageenans, algic acid, alginates, pectin, inulin, xanthan gum and mixtures of two or more of the substances mentioned.

The cosmetic or pharmaceutical compositions according to the invention can be produced by conventional processes known per se, such that compound(s) of the general formula 1 and diisopropyl adipate, both incorporated into (topical) cosmetic or pharmaceutical compositions which (in addition to the aforementioned effects) can also be used for the treatment, care and/or cleansing of the skin or hair.

Compositions, in particular (topical) cosmetic products, according to the present invention can advantageously additionally comprise suitable auxiliary substances and additives, such as, for example:

preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxyacids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, anticellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

The (in particular topical) cosmetic or pharmaceutical products according to the invention can comprise cosmetic auxiliary substances and additives such as are conventionally used in such formulations, e.g. sunscreen agents, preservatives, bactericides, fungicides, virucides, cooling active compounds, insect repellents (e.g. DEET, IR 3225), plant extracts, plant parts, antiinflammatory active compounds, substances which accelerate wound healing (e.g. chitin or chitosan and derivatives thereof), film-forming substances (e.g. polyvinylpyrrolidones or chitosan or derivatives thereof), antioxidants, vitamins, 2-hydroxycarboxylic acids (e.g. citric acid, malic acid, L-, D- or d-lactic acid), skin-colouring agents (e.g. walnut extracts or dihydroxyacetone), active compounds for promoting hair growth or inhibiting hair growth, skin care compositions (e.g. cholesterol, ceramides, pseuodceramides), softening, moisturizing and/or humectant substances, fats, oils, saturated fatty acids, mono- or polyunsaturated fatty acids, α-hydroxy acids, polyhydroxy-fatty acids or derivatives thereof, waxes or other conventional constituents of a cosmetic or dermatological formulation, such as alcohols, polyols, polymers, foam stabilizers, electrolytes, organic solvents, silicone derivatives of chelating agents (e.g. ethylenediaminetetraacetic acid and derivatives), antidandruff active compounds (e.g. climbazole, ketoconazole, piroctonoleamine, zinc pyrithione), hair care agents, perfumes, substances for preventing foaming, dyestuffs, pigments which have a colouring action, thickening agents (advantageously silicon dioxide, aluminium silicates, such as e.g. bentonites, polysaccharides or derivatives thereof, e.g. hyaluronic acid, guar bean flour, xanthan gum, hydroxypropylmethylcellulose or allulose derivatives, particularly advantageously polyacrylates, such as e.g. Carbopols or polyurethanes), surface-active substances and emulsifiers.

Auxiliary substances and additives (excluding water) can generally be included in products according to the present invention in quantities of 1 to 95 wt. %, preferably 5 to 70 wt. %, more preferably 5 to 50 wt. %, in each case based on the total weight of the product. The amounts of cosmetic or dermatological auxiliary agents and additives and perfume to be used in each case can easily be determined by the person skilled in the art by simple trials, depending on the nature of the particular product.

According to one aspect of the invention, the products or, respectively, compositions according to the present invention preferably contain water in a quantity of up to 98 wt. %, preferably 10 to 95 wt. %, more preferably 25 to 90 wt. %, even more preferably 40 to 90 wt. %, in each case based on the total weight of the product or, respectively, composition.

The products or, respectively, compositions according to the invention can also comprise further antioxidants, wherein it is possible for all the antioxidants which are suitable or usual for cosmetic and/or dermatological uses to be used. The antioxidants are advantageously chosen from the group consisting of:
amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), (metal) chelators, e.g. α-hydroxy-fatty acids, palmitic acid, phytic acid, lactoferrin, α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glycosides, such as e.g. 6-O-acyl-2-O-α-D-glucopyranosyl-L-ascorbic acid, 6-O-acyl-2-O-β-D-glucopyranosyl-L-ascorbic acid, 2-O-α-D-glucopyranosyl-L-ascorbic acid or 2-O-β-D-glucopyranosyl-L-ascorbic acid), tocopherols and derivatives thereof (e.g. vitamin E acetate), vitamin A and derivatives thereof (vitamin A palmitate) as well as coniferylbenzoate of benzoin resin, rutic acid and derivatives thereof, α-glucosylrutin, quercetin and derivatives thereof, rosemary acid, carnosol, carnosol acid, resveratrol, caffeic acid and derivatives thereof, sinapic acid and derivatives thereof, ferulic acid and derivatives thereof, furfurylideneglucitol, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and derivatives (salts, esters, ethers, sugars, nucleotides, nucleosides, peptides and lipids) of these active compounds mentioned or antioxidatively active extracts or fractions from plants, such as e.g. green tea, rooibos, honeybush, grape, rosemary, sage, Melissa, thyme, lavender, olive, oats, cocoa, ginkgo, ginseng, liquorice, honeysuckle, Sophora, Pueraria, Pinus, Citrus, *Phyllanthus emblica* or St. John's wort.

The products or, respectively, compositions according to the present invention can also comprise physiological warming (heating) agents. Such physiological warming agents preferably are selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, zingerone, capsaicin, dihydrocapsaicin, nordihydrocapsaicin, homocapsaicin, homodihydrocapsaicin, iso-propyl alcohol, iso-amylalcohol, benzyl alcohol, eugenol, cinnamon oil, cinnamic aldehyde, and mixtures thereof.

The products or, respectively, compositions according to the invention may advantageously comprise at least one UVA filter and/or at least one UVB filter and/or at least one inorganic pigment. In this context, the formulations can be in various forms such as are conventionally employed e.g. for sunscreen formulations for protecting the skin and hair against ultraviolet radiation. They can thus form e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol. In this context, the total amount of UV-filter substances is from 0.01 wt. % to 40 wt. %, preferably 0.1 to 10 wt. %, in particular 1.0 to 5.0 wt. %, based on the total weight of the product or, respectively, composition.

Advantageous UV filters are e.g.:
p-aminobenzoic acid, p-aminobenzoic acid ethyl ester (25 mol) ethoxylated, p-dimethylaminobenzoic acid 2-ethylhexyl ester, p-aminobenzoic acid ethyl ester (2 mol) N-propoxylated, p-aminobenzoic acid glycerol ester, salicylic acid homomenthyl ester (homosalate) (Neo Heliopan®HMS), salicylic acid 2-ethylhexyl ester (Neo Heliopan®OS), triethanolamine salicylate, 4-isopropylbenzyl salicylate, anthranilic acid menthyl ester (Neo Heliopan®MA), diisopropylcinnamic acid ethyl ester, p-methoxycinnamic acid 2-ethylhexyl ester (Neo Heliopan®AV), diisopropylcinnamic acid methyl ester, p-methoxycinnamic acid isoamyl ester (Neo Heliopan®E 1000), p-methoxycinnamic acid diethanolamine salt, p-methoxycinnamic acid isopropyl ester, 2-ethylhexyl 2-cyano-3,3-diphenylacrylate (Neo Heliopan©303), ethyl 2-cyano-3,3'-diphenylacrylate, 2-phenylbenzimidazolesulfonic acid and salts (Neo Heliopan®Hydro), 3-(4'-trimethylammonium)-benzylidene-bornan-2-one methyl-sulfate, terephthalylidene-dibornanesulfonic acid and salts (Mexoryl®SX), 4-t-butyl-4'-methoxy-dibenzoylmethane (avobenzone)/(Neo Heliopan®357), β-Imidazole-4(5)-acrylic acid (urocanic acid), 2-hydroxy-4-methoxybenzophenone (Neo Heliopan®BB), 2-hydroxy-4-methoxybenzophenone-5-sulfonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, 3-(4'-sulfo)benzylidene-bornan-2-one and salts, 3-(4'-methylbenzylidene)-d,l-camphor (Neo Heliopan®MBC), 3-benzylidene-d,l-camphor, 4-isopropyldibenzoylmethane, 2,4,6-trianilino-(p-carbo-2'-ethylhexyl-1'-oxy)-1,3,5-triazine, phenylene-bis-benzimidazyl-tetrasulfonic acid disodium salt (Neo Heliopan®AP), 2,2'-(1,4-phenylene)-bis-(1H-benzimidazole-4,6-disulfonic acid), monosodium salt, N-[(2 and 4)-[2-(oxoborn-3-ylidene)methyl]benzyl]-acrylamide polymer, phenol, -(2H-benzotriazol-2-yl)-4-methyl-6-(2-methyl-3(1,3,3,3-tetramethyl-1-(trimethylsilyl)-oxy)-disiloxanyl)-propyl), (Mexoryl®XL), 4,4'-[(6-[4-(1,1-dimethyl)-aminocarbonyl)-phenylamino]-1,3,5-triazine-2,4-diyl)diimino]-bis-(benzoic acid 2-ethylhexyl ester) (Uvasorb®HEB), 2,2'-methylene-bis-(6-(2H-benzotriazol-2-yl)-4-(1,1,3,3-tetramethylbutyl)-phenol), (Tinosorb®M), 2,4-bis-[4-(2-ethylhexyloxy)-2-hydroxyphenyl]-1,3,5-triazine, benzylidene malonate-polysiloxane (Parsol®SLX), glyceryl ethylhexanoate dimethoxycinnamate, disodium 2,2'-dihydroxy-4,4'-dimethoxy-5,5'-disulfo-benzophenone, dipropylene glycol salicylate, sodium hydroxymethoxybenzophenone-sulfonate, 4,4',4-(1,3,5-triazine-2,4,6-triyltriimino)-tris-benzoic acid tris(2-ethylhexyl ester) (Uvinul®T150), 2,4-bis-[{(4-(2-ethyl-hexyloxy)-2-hydroxy}-phenyl]-6-(4-methoxyphenyl)-1,3,5-triazine, (Tinosorb®S), 2,4-bis-[{(4-(3-sulfonato)-2-hydroxy-propyloxy)-2-hydroxy}-phenyl]-6-(4-methoxyphenyl)-1,3,5-triazine sodium salt, 2,4-bis-[{(3-(2-propyloxy)-2-hydroxy-propyloxy)-2-hydroxy}-phenyl]-6-(4-methoxy-phenyl)-1,3,5-triazine, 2,4-bis-[{4-(2-ethyl-hexyloxy)-2-hydroxy}-phenyl]-6-[4-(2-methoxyethyl-carbonyl)-phenylamino]-1,3,5-triazine, 2,4-bis-[{4-(3-(2-propyloxy)-2-hydroxy-propyloxy)-2-hydroxy}-phenyl]-6-[4-(2-ethylcarboxyl)-phenylamino]-1,3,5-triazine, 2,4-bis-[{4-(2-ethyl-hexyloxy)-2-hydroxy}-phenyl]-6-(1-methyl-pyrrol-2-yl)-1,3,5-triazine, 2,4-bis-[{4-tris-(trimethylsiloxy-silylpropyloxy)-2-hydroxy}-phenyl]-6-(4-methoxyphenyl)-1,3,5-triazine, 2,4-bis-[{4-(2"-methylpropenyloxy)-2-hydroxy}-phenyl]-6-(4-methoxyphenyl)-1,3,5-triazine, 2,4-bis-[{4-(1',1',1',3',5',5',5'-heptamethylsiloxy-2"-methyl-propyloxy)-2-hydroxy}-phenyl]-6-(4-methoxyphenyl)-1,3,5-triazine, 2-(4-diethylamino-2-hydroxybenzoyl)-benzoic acid hexyl ester (Uvinul® A Plus) and indanylidene compounds according to DE 100 55 940 (=WO 02/38537).

In this context, UV absorbers which are particularly suitable for combination are p-aminobenzoic acid, 3-(4'-trimethylammonium)-benzylidene-bornan-2-one methyl-sulfate, salicylic acid homomenthyl ester (Neo Heliopan®HMS), 2-hydroxy-4-methoxy-benzophenone (Neo Heliopan®BB), 2-phenylbenzimidazolesulfonic acid (Neo Heliopan®Hydro), terephthalylidene-dibornanesulfonic acid and salts (Mexoryl®SX), 4-tert-butyl-4'-methoxydibenzoylmethane (Neo Heliopan®357), 3-(4'-sulfo)benzylidene-bornan-2-one and salts, 2-ethylhexyl 2-cyano-3,3-diphenylacrylate (Neo Heliopan©303), N-[(2 and 4)-[2-(oxoborn-3-ylidene)methyl]benzyl]-acrylamide polymer, p-methoxycinnamic acid 2-ethylhexyl ester (Neo Heliopan®AV), p-aminobenzoic acid ethyl ester (25 mol) ethoxylated, p-methoxycinnamic acid isoamyl ester (Neo Heliopan®E1000), 2,4,6-trianilino-(p-carbo-2'-ethylhexyl-1'-oxy)-1,3,5-triazine (Uvinul®T150), phenol, 2-(2H-benzotriazol-2-yl)-4-methyl-6-(2-methyl-3(1,3,3,3-tetramethyl-1-(trimethylsilyl)-oxy)-disiloxanyl)-propyl), (Mexoryl®XL), 4,4'-[(6-[4-(1,1-dimethyl)-aminocarbonyl)-phenylamino]-1,3,5-triazine-2,4-diyl)-diimino]-bis-(benzoic acid 2-ethylhexyl ester), (UvasorbHEB), 3-(4'-methylbenzylidene)-d,l-camphor (Neo Heliopan®MBC), 3-benzylidenecamphor, salicylic acid 2-ethylhexyl ester (Neo Heliopan®OS), 4-dimethylaminobenzoic acid 2-ethylhexyl ester (Padimate 0), hydroxy-4-methoxy-benzophenone-5-sulfonic acid and Na salt, 2,2'-methylene-bis-(6-(2H-benzotriazol-2-yl)-4-(1,1,3,3-tetramethylbutyl)-phenol), (Tinosorb®M), phenylene-bis-benzimidazyl-tetrasulfonic acid disodium salt (Neo Heliopan®AP), 2,4-bis-[{(4-(2-ethyl-hexyloxy)-2-hydroxy}-phenyl]-6-(4-methoxyphenyl)-1,3,5-triazine, (Tinosorb®S), benzylidene malonate-polysiloxane (Parsol®SLX), menthyl anthranilate (Neo Heliopan®MA), 2-(4-diethylamino-2-hydroxybenzoyl)-benzoic acid hexyl ester (Uvinul® A Plus) and indanylidene compounds according to DE 100 55 940 (=WO 02/38537).

Advantageous inorganic sunscreen pigments are finely dispersed metal oxides and metal salts, for example titanium dioxides, zinc oxide (ZnO), iron oxides (e.g. $Fe_2O_3$), aluminium oxide ($Al_2O_3$); cerium oxides (e.g. $Ce_2O_3$), manganese oxides (e.g. MnO), zirconium oxide ($ZrO_2$), silicon oxide ($SiO_2$), mixed oxides of the corresponding metals and mixtures of such oxides, barium sulfate and zinc stearate. They are particularly preferably pigments based on $TiO_2$ or zinc oxide. In preferred embodiments, the particles have an average diameter of less than 100 nm, preferably between 5 and 50 nm and particularly preferably between 15 and 30 nm. They can have a spherical shape, but those particles which have an ellipsoid shape or a shape which deviates otherwise from the spherical can also be employed. The pigments can also be in a form treated on the surface, i.e. hydrophilized or hydrophobized. Typical examples are coated titanium dioxides, such as e.g. titanium dioxide T 805 (Degussa) or Eusolex® T2000 (Merck), or coated zinc oxide, such as e.g. Zinc Oxide NDM. In this context, possible hydrophobic coating agents are, above all, silicones, and in this case specifically trialkoxyoctysilanes or simethicone. So-called micro- or nanopigments are preferably employed in sunscreen compositions. Zinc micro- or nanopigments are preferably employed.

The total amount of inorganic pigments, in particular hydrophobic inorganic micropigments, in the finished products or, respectively, compositions is advantageously in the range of from 0.1 to 30 wt. %, preferably 0.1 to 10.0 wt. %, in particular 0.5 to 6.0 wt. %, based on the total weight of the product or, respectively, composition.

Products or, respectively, compositions can also comprise (further) active compounds and active compound combinations against ageing of the skin and wrinkles. According to the invention, all the active compounds against ageing of the skin and wrinkles which are suitable or usual for cosmetic and/or dermatological uses can be used here. Advantageous active compounds against ageing of the skin and wrinkles in this respect are soya protein or protein hydrolysates, soya isoflavones, hydrolyzed rice protein, hydrolysed hazelnut protein, oligopeptides from hydrolysed Hibiscus esculentus extract, wheat protein, β-glucans, e.g. from oats, and derivatives thereof, glycoproteins, ursolic acid and its salts, betulin, betulic acid and its salts, retinol, retinol palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, creatine or other synthetic or natural active compounds against ageing of the skin and wrinkles, it being possible for the latter also to be used in the form of an extract from plants, such as e.g. green tea, *Rubus fruticosus, Sanguisorba officinalis, Centella asiatica, Ribes nigrum, Passiflora incarnata, Filipendula ulmaria, Phyllanthus emblica, Potentilla* species, okra, algae, evening primrose, pomegranate, lady's mantle, rosemary, sage, Aloe species, *Echinacea*, birch, apple or soya.

Substances which are particularly preferred for use as further active compounds against ageing of the skin are β-glucans, and 1,3-1,4-linked β-glucan from oats, *Rubus fruticosus* extract or wheat protein is particularly preferred.

The products or, respectively, compositions according to the invention can also comprise active compounds which stimulate shading or tanning of the skin and hair in a chemical or natural manner. A faster action based on synergistic effects is thereby achieved. Substances which are particularly preferred in this context are substrates or substrate analogues of tyrosinase, such as L-tyrosine, L-DOPA or L-dihydroxyphenylalanine, stimulators of tyrosinase activity or expression, such as theophylline, caffeine, propiomelanocortin peptides, such as ACTH, alpha-MSH, peptide analogues thereof and other substances which bind to the melanocortin receptor, peptides, such as Val-Gly-Val-Ala-Pro-Gly, Lys-Ile-Gly-Arg-Lys or Leu-Ile-Gly-Lys, purines, pyrimidines, folic acid, copper salts, such as copper gluconate, chloride or pyrrolidonate, flavonoids, flavanone glycosides, such as naringin and hesperidin, melanin derivatives, such as Melasyn-100 and MelanZe, diacylglycerols, aliphatic or cyclic diols, psoralene, prostaglandins and analogues thereof, activators of adenylate cyclase and compounds which activate the transfer of melanosomes into keratinocytes, such as serine proteases or extracts from plants and plant parts of the *Chrysanthemum* species or *Sanguisorba* species, walnut extracts, urucum extracts, rhubarb extracts, erytrulose and dihydroxyacetone.

The products or, respectively, compositions according to the invention can also be employed in combination with skin-lightening active compounds. According to the invention, all the skin-lightening active compounds which are suitable or usual for cosmetic and/or dermatological uses can be used here. Advantageous skin-lightening active compounds in this respect are kojic acid (5-hydroxy-2-hydroxymethyl-4-pyranone), kojic acid derivatives, such as e.g. kojic acid dipalmitate, arbutin, ascorbic acid, ascorbic acid derivatives, hydroquinone, hydroquinone derivatives, resorcinol, sulfur-containing molecules, such as e.g. cysteine, alpha-hydroxy acids (e.g. citric acid, lactic acid, malic acid) and derivatives thereof, N-acetyl-tyrosine and derivatives, undecenoylphenylalanine, gluconic acid, 4-alkylresorcinols, 4-(1-phenylethyl)-1,3-benzenediol, chromone derivatives, such as aloesin, flavonoids, thymol derivatives, 1-aminoethylphosphinic acid, thiourea derivatives, ellagic acid, nicotinamide, zinc salts, such as e.g. zinc chloride or gluconate, thujaplicin and derivatives, triterpenes, such as maslic acid, sterols, such as ergosterol, benzofuranones, such as senkyunolide, vinyl- and ethylguaiacol, inhibitors of nitrogen oxide synthesis, such as e.g. L-nitroarginine and derivatives thereof, 2,7-dinitroindazole or thiocitrullin, metal chelators (e.g. α-hydroxy-fatty acids, palmitic acid, phytic acid, lactoferrin, humic acid, bile acid, bile extracts, bilirubin, biliverdin, EDTA, EGTA and derivatives thereof), retinoids, soya milk, serine protease inhibitors or liponic acid or other synthetic or natural active compounds for lightening of the skin and hair, the latter also being used in the form of an extract from plants, such as e.g. bearberry extract, rice extract, liquorice root extract or constituents concentrated therefrom, such as glabridin or licochalcone A, *Artocarpus* extract, extract from *Rumex* and *Ramulus* species, extracts from pine species (*Pinus*) and extracts from *Vitis* species or stilbene derivatives concentrated therefrom, and extract from Saxifraga, mulberry, Scutelleria or/and grape.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophylline and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, zinc diglycinate (Zn(Gly)2), manganese(II) bicarbonate complexes ("pseudocatalases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases, extracts of plants and plant parts of the *chrysanthemum* species, *sanguisorba* species, walnut extracts, urucum extracts, rhubarb extracts, trehalose, erythrulose and dihydroxyacetone. Flavonoids which bring about skin and hair tinting or tanning (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

Products or, respectively, compositions according to the invention can advantageously also comprise moisture retention regulators. The following substances e.g. are used as moisture retention regulators ("moisturizers"): sodium lactate, urea and derivatives, alcohols, glycerol, diols, such as propylene glycol, 1,2-pentanediol, 1,2-hexanediol and 1,2-octanediol, collagen, elastin or hyaluronic acid, diacyl adipates, petrolatum, urocanic acid, lecithin, panthenol, phytantriol, lycopene, (pseudo-)ceramides, glycosphingolipids, cholesterol, phytosterols, chitosan, chondroitin sulfate, lanolin, lanolin esters, amino acids, alpha-hydroxy acids (e.g. citric acid, lactic acid, malic acid) and derivatives thereof, mono-, di- and oligosaccharides, such as, for example, glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts.

Products or, respectively, compositions according to the invention can also be employed together with osmolytes.

Osmolytes which may be mentioned by way of example are: substances from the group consisting of sugar alcohols (myo-inositol, mannitol, sorbitol), quaternary amines, such as taurine, choline, betaine, betaine-glycine and ectoin, diglycerol phosphate, phosphorylcholine, glycerophosphorylcholines, amino acids, such as glutamine, glycine, alanine, glutamate, aspartate or proline, phosphatidylcholine, phosphatidylinositol and inorganic phosphates, as well as polymers of the compounds mentioned, such as proteins, peptides, poly-amino acids and polyols. All osmolytes at the same time have a skin-moisturizing action.

Products or, respectively, compositions according to the invention can advantageously also comprise vitamins and vitamin precursors, it being possible for all the vitamins and vitamin precursors which are suitable or usual for cosmetic and/or dermatological uses to be used.

The products or, respectively, compositions according to the invention moreover can also preferably comprise perspiration-inhibiting active compounds (antiperspirants) and odour absorbers. Perspiration-inhibiting active compounds which are employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning. Alongside aluminium salts, further substances are also possible, such as, for example, a) protein-precipitating substances, such as, inter alia, formaldehyde, glutaraldehyde, natural and synthetic tannins and trichloro-acetic acid, which bring about blockage of the sweat glands on the surface, b) local anaesthetics (inter alia dilute solutions of e.g. lidocaine, prilocaine or mixtures of such substances), which eliminate sympathetic supply of the sweat glands by blockade of the peripheral nerve pathways, c) zeolites of the X, A or Y type, which, alongside the reduction in secretion of perspiration, also function as adsorbents for bad odours, and d) botulinus toxin (toxin of the bacterium *Chlostridium botulinum*), which is also employed in cases of hyperhidrosis, a pathologically increased secretion of perspiration, and the action of which is based on an irreversible blocking of the release of the transmitter substance acetylcholine, which is relevant for secretion of perspiration.

Odour absorbers are, for example, the laminar silicates described in DE 40 09 347, and of these in particular montmorillonite, kaolinite, nontronite, saponite, hectorite, bentonite and smectite, and furthermore, for example, zinc salts of ricinoleic acid. These likewise include deodorants, bactericidal or bacteriostatic deodorizing substances, such as e.g. hexachlorophene, 2,4,4'-trichloro-2' hydroxydiphenyl ether (Irgasan), 1,6-di-(4-chlorophenylbiguanido)-hexane (chlorhexidine) and 3,4,4'-trichlorocarbanilide, as well as the active agents described in DE 37 40 186, DE 39 38 140, DE 42 04 321, DE 42 29 707, DE 42 29 737, DE 42 37 081, DE 43 09 372 and DE 43 24 219, and cationic substances, such as e.g. quaternary ammonium salts, and odour absorbers, such as e.g. ®Grillocin (combination of zinc ricinoleate and various additives) or triethyl citrate, optionally in combination with ion exchange resins.

In various cases it may also be advantageous to use substances which are chiefly employed for inhibition of the growth of undesirable microorganisms. In this respect, alongside conventional preservatives, further active compounds which are worth mentioning, alongside the large group of conventional antibiotics, are, in particular, the products relevant for cosmetics, such as triclosan, climbazole, zinc pyrithione, ichthyol, Octopirox (1-hydroxy-4-methyl-6-(2,4,4-trimethylpentyl)-2(1H)-pyridone, 2-aminoethanol), chitosan, farnesol, octoxyglycerol, glycerol monolaurate, arylalkyl alcohols, such as e.g. phenylethyl alcohol, 3-phenyl-1-propanol, veticol or muguet alcohol, polyglycerol esters, such as e.g. polyglyceryl 3-caprylates, and aliphatic diols, such as e.g. 1,2-decanediol, or combinations of the substances mentioned, which are employed, inter alia, against underarm odour, foot odour or dandruff formation.

Products or, respectively, compositions according to the invention can in numerous cases also advantageously comprise preservatives. Preservatives which are preferably chosen here are those such as benzoic acid and its esters and salts, 4-hydroxybenzoic acid and its esters (INCI: Parabens, preferably methylparaben, ethylparaben, butylparaben, propylparaben and/or isobutylparaben) and salts, propionic acid and its esters and salts, salicylic acid and its esters and salts, 2,4-hexadienoic acid (sorbic acid) and its esters and salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylenediguanide)hydrochloride, 2-phenoxyethanol, hexamethylenetetramine, 1-(3-chloroallyl)-3,5,7-triaza-1-azonia-adamantane chloride, 1-(4-chloro-phenoxy)-1-(1H-imidazol-1-yl)-3,3-dimethyl-2-butanone, 1,3-bis-(hydroxy-methyl)-5,5-dimethyl-2,4-imidazolidin-edione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H)-isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$) trimethyl-ammonium bromide and chloride, 4,4-dimethyl-1,3-oxazolidine, N-hydroxymethyl-N-(1,3-di (hydroxymethyl)-2,5-dioxoimidazolidin-4-yl)-N'-hydroxymethylurea, 1,6-bis(4-amidino-phenoxy)-n-hexane and its salts, glutaraldehyde, 5-ethyl-1-aza-3,7-dioxabicyclo(3.3.0) octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate.

Products or, respectively, compositions according to the invention can also be in the form of emulsions.

The oily phase can advantageously be chosen from the following substance group:
mineral oils, mineral waxes
fatty oils, fats, waxes and other natural and synthetic fat substances, preferably esters of fatty acids with alcohols of low C number, e.g. with isopropanol, propylene glycol or glycerol, or esters of fatty alcohols with alkanoic acids of low C number or with fatty acids;
alkyl benzoates;
silicone oils, such as dimethylpolysiloxanes, diethylpolysiloxanes, diphenylpolysiloxanes and mixed forms thereof.

Compounds which can advantageously be employed are (a) esters of saturated and/or unsaturated branched and/or unbranched alkane carboxylic acids having a chain length of from 3 to 30 C atoms and saturated and/or unsaturated, branched and/or unbranched alcohols having a chain length of from 3 to 30 C atoms, (b) esters of aromatic carboxylic acids and saturated and/or unsaturated, branched and/or unbranched alcohols having a chain length of from 3 to 30 C atoms. Preferred ester oils are isopropyl myristate, isopropyl palmitate, isopropyl stearate, isopropyl oleate, n-butyl stearate, n-hexyl-laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, 2-octyldodecyl palmitate, stearyl isononanoate, palmityl isononanoate, cetearyl isononanoate, stearyl nonanoate, palmityl nonanoate, cetearyl nonanoate, palmityl 3,5,5-trimethylhexanoate, stearyl 3,5,5-trimethylhexanoate, cetearyl 3,5,5-trimethylhexanoate, oleyl oleate, oleyl erucate, erucyl oleate, erucyl erucate and synthetic, semi-synthetic and natural mixtures of such esters, e.g. jojoba oil.

The oily phase can furthermore advantageously be chosen from the group consisting of branched and unbranched hydrocarbons and waxes, silicone oils and dialkyl ethers, the group consisting of saturated or unsaturated, branched or unbranched alcohols, and the fatty acid triglycerides, namely the triglycerol esters of saturated and/or unsaturated, branched and/or unbranched alkanecarboxylic acids having a chain length of from 8 to 24, in particular 12 to 18 C atoms. The fatty acid triglycerides can advantageously be chosen from the group consisting of synthetic, semi-synthetic and natural oils, e.g. olive oil, sunflower oil, soya oil, groundnut oil, rapeseed oil, almond oil, palm oil, coconut oil, palm kernel oil and more of the like. Any desired blends of such oil and wax components can also advantageously be employed. In some cases, it is also advantageous to employ waxes, for example cetyl palmitate, as the sole lipid component of the oily phase, and the oily phase is advantageously chosen from the group which consists of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oily phase can furthermore have a content of cyclic or linear silicone oils or consist entirely of such oils, it being advantageous to use an additional content of other oily phase components in addition to the silicone oil or silicone oils. Cyclomethicone (e.g. decamethylcyclopentasiloxane) can advantageously be employed as a silicone oil. However, other silicone oils, for example undecamethylcyclotrisiloxane, polydimethylsiloxane and poly(methyl-phenylsiloxane), can also advantageously be used. Mixtures of cyclomethicone and isotridecyl isononanoate and of cyclomethicone and 2-ethylhexyl isostearate are furthermore particularly advantageous.

Formulations in the form of an emulsion which comprise a formulation according to the invention advantageously comprise one or more emulsifiers. O/W emulsifiers can advantageously be chosen, for example, from the group consisting of further polyethoxylated but also polypropoxylated or further polyethoxylated and polypropoxylated products not mentioned as preferred polyethoxylated products used as component of compositions according to the present invention.

Polyethoxylated or polypropoxylated or polyethoxylated and polypropoxylated O/W emulsifiers employed are particularly advantageously chosen from the group consisting of substances having HLB values of 11-18, very particularly advantageously having HLB values of 14.5-15.5, if the O/W emulsifiers contain saturated radicals R and R'. If the O/W emulsifiers contain unsaturated radicals R and/or R', or isoalkyl derivatives are present, the preferred HLB value of such emulsifiers can also be lower or higher. It is of advantage to choose the fatty alcohol ethoxylates from the group consisting of ethoxylated stearyl alcohols, cetyl alcohols and cetyl stearyl alcohols (cetearyl alcohols).

Advantageous W/O emulsifiers which can be employed are: fatty alcohols having 8 to 30 carbon atoms, monoglycerol esters of saturated and/or unsaturated, branched and/or unbranched alkanecarboxylic acids having a chain length of from 8 to 24, in particular 12 to 18 C atoms, diglycerol esters of saturated and/or unsaturated, branched and/or unbranched alkanecarboxylic acids having a chain length of from 8 to 24, in particular 12 to 18 C atoms, monoglycerol ethers of saturated and/or unsaturated, branched and/or unbranched alcohols having a chain length of from 8 to 24, in particular 12 to 18 C atoms, diglycerol ethers of saturated and/or unsaturated, branched and/or unbranched alcohols having a chain length of from 8 to 24, in particular 12 to 18 C atoms, propylene glycol esters of saturated and/or unsaturated, branched and/or unbranched alkanecarboxylic acids having a chain length of from 8 to 24, in particular 12 to 18 C atoms and sorbitan esters of saturated and/or unsaturated, branched and/or unbranched alkanecarboxylic acids having a chain length of from 8 to 24, in particular 12 to 18 C atoms.

Products or, respectively, compositions according to the invention for cosmetic (topical) prophylactic (preventive) treatment of the skin can regularly comprise a high content of care substances. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, oat oil, sperm oil, beef tallow, neat's foot oil and lard, and optionally further care constituents, such as, for example, fatty alcohols having 8-30 C atoms. The fatty alcohols here can be saturated or unsaturated and linear or branched. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and Guerbet alcohols thereof, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as e.g. beef tallow, groundnut oil, colza oil, cottonseed oil, soya oil, sunflower oil, palm kernel oil, linseed oil, maize oil, castor oil, rape oil, sesame oil, cacao butter and coconut fat, can furthermore be employed.

Preferred embodiments and further aspects of the present invention emerge from the attached claims and the following examples, the examples not being intended to limit the invention. Unless indicated otherwise, all data, in particular percentages, refer to the weight.

EXAMPLES OF THE DISCLOSURE

Example 1: Test Results

Example 1.1: Cytotoxicity Assay

The TOX8 (Sigma Aldrich) Kit was used to determine cytotoxicity retinoic acid, 3,3-dimethyl-2-oxobutyl ester (MDI 101) on 3T3 swiss albino mouse fibroblasts. The 3T3 were cultivated in DMEM medium (Capricorn) including 10% FBS, 1% Penicillin/Streptomycin and 100 nM sodium selenite at 37° C. and 5% CO2. For the cytotoxicity experiment, 3T3 were seeded into 96-well microtiter plate. After 24 hours incubation and a confluence of 30 to 40% the cells were treated with MDI 101 in four different concentrations for 48 h. Test substance was pre-diluted in DMSO, further dilutions were performed in equal medium with 5% FBS. After 48 h a microscopic estimation was carried out and the cells were incubated with TOX8-Kit for two hours at 37° C. and 5% CO2. The absorbance of a converted dye was measured by spectrophotometry at a wavelength of 600 nm. Bioreduction of the dye reduces the amount of its oxidized form (blue) and concomitantly increases the fluorescent intermediate (red), wherein the mechanism and applicability of the test is independent of the cell type. Cell viability was analyzed relative to the solvent-control. The inhibitory concentrations for 50% viability (IC50) and 80% (IC20) were calculated.

The specific concentration of MDI 101 in the cell culture medium, which is lethal for 20% (IC20) and for 50% (IC50) of living cells was determined:

| Substance | IC20 [mM] | IC50 [mM] |
|---|---|---|
| MDI 101 | 0.171 | 0.263 |

Example 1.2: Determination of Anti-Oxidative Capacity

For the determination of the anti-oxidative capacity, the ABTS+-Assay was performed. The assay principle bases on the reduction and the involved decolourization of the green coloured cationic radical 2,2'-Azinobis(3-ethylbenzothiazoline 6-sulfonic acid) (ABTS+) by antioxidants. The decolourization can be measured spectrophotometrically at 734 nm.

The determination of the anti-oxidative capacity is performed in 96-well microplates from Nunc (Wiesbaden, Germany) and with the microplate reader "Spark" from Tecan (Crailsheim, Germany).

Samples were incubated for 10 min at 30° C. with the 2,2'-Azinobis-(3-ethylbenzothiazoline-6-sulfonate (ABTS+) radical cation (Sigma, St. Louis, USA) prepared by reaction of ABTS+ with potassium persulfate. As a positive control Trolox is always co-tested. The degree of decolourization was determined spectrophotometrically at 734 nm by triple determination each. Results are mean values from 2 independent experiments with quadruple determinations each.

The antioxidative capacity is expressed in $IC_{50}$ values (concentration that scavenges 50% of the cationic radical relative to the untreated ABTS+ solution), which can be determined by a trend calculation.

| Substance | Concentration [µM] | Mean inhibition [%] | Mean deviation [%] |
|---|---|---|---|
| MDI 101 | 500 | 96.4 | 0.83 |
|  | 250 | 83.3 | 4.06 |
|  | 50 | 27.3 | 1.82 |
|  | 25 | 17.7 | 0.04 |
|  | 2 | 8.8 | 1.08 |

Example 1.3: Determination of Oxidative Stress

For the quantification of intracellular radicals, the dichlorofluorescein (DCF) assay was performed. The cell-permeant 2',7'-dichlorodihydrofluorescein diacetate (H2DCFDA) (also known as dichlorofluores cin diacetate) is a chemically reduced form of fluorescein used as an indicator for reactive oxygen species (ROS) in cells. By intracellular esterases and oxidation, the nonfluorescent H2DCFDA is converted to the highly fluorescent 2',7'-dichlorofluorescein (DCF). The nonfluorescent fluorescin (2',7'-dichlorofluorescein diacetate (DCFH-DA) pass the cell membranes. In the cytoplasm, it is splitted by intracellular esterases and cannot leave out of the cell in this form. The oxidation by intracellularly existing ROS (reactive oxygen species) modifies the molecule so that will become DCF and emit fluorescence.

Determination of the anti-oxidative capacity is performed in 96-well microplates from Nunc (Wiesbaden, Germany) and with the microplate reader "Spark" from Tecan (Crailsheim, Germany).

Cells are seeded in a black 96 well microplate with transparent bottom and incubated at 37° C. After 24 hours the supernatant is decanted and fresh media with 0.1% FBS is succeded. Further 24 hours later the supernatant is decanted again and the test samples are added and incubated for 24 hours. Varying concentrations of MDI 101 in the cell culture medium were tested. As a positive control Trolox is always co-tested. Then the DCF Assay is performed and the fluorescence is measured from bottom of well at EX/EM 485/528 nm. The antioxidative capacity is expressed in percent, which can be determined by rule of proportion in combination with the control.

| Substance | Concentration [µM] | ROS mean value [%] | ROS reduction [%] |
|---|---|---|---|
| MDI 101 | 0.02 | 23 | 77.5 |
|  | 0.002 | 75 | 25 |

An anti-oxidative effect for MDI 101 was thus observed for concentrations which should have no cytotoxic effect.

Example 1.4: Proliferation Assay

To evaluate the pro-proliferative activity of MDI 101, the CyQUANT® Direct Cell Proliferation Assay was performed. The CyQUANT® Direct assay is based on a cell-permeant DNA-binding dye in combination with a background suppression reagent. As DNA content is highly regulated, cell number estimates are very accurate. The masking dye blocks staining of dead cells and cells with compromised cell membranes, causing only staining of healthy cells. Therefore, the CyQUANT® Direct assay measures proliferation as well as cytotoxicity. The fluorescence can be measured spectrophotometrically from bottom of well with standard green filter sets or wavelengths (EX/EM 508/527 nm).

The proliferation capacity is performed in black 96-well microplates from Corning (Germany) and with the microplate reader "Spark" from Tecan (Crailsheim, Germany).

Cells are seeded in a black 96 well microplate with transparent bottom and incubated at 37° C. and 5% $CO_2$. After 24 hours the supernatant is decanted and the samples are added in fresh media with 6% FBS. As a positive control KGF is always co-tested. Further 72 hours later the 2× Reaction Reagent is added in an equal volume to the cells incubated for 1 hour. Then the CyQUANT® Direct assay is performed and the fluorescence is measured from bottom of well at EX/EM 508/527 nm.

The proliferation probability is expressed in percent, which can be determined by rule of proportion in combination with the control.

| Concentration of MDI 101 [mM] | Mean proliferation compared to control (100%) [%] |
|---|---|
| 0.00005 | 125 |

Example 1.5: 3D Epidermis Models

The three-dimensional (3D) epidermis model enables an essential way to simulate experiment conditions that are more comparable with human skin. With such 3D assays significant information is obtained about the complex stratification and terminal differentiation process of keratinocytes in a multilayered epidermal tissue with barrier functionality. Thickness of the Epidermis:

Furthermore, paraffin sectioning and a H&E and Ki67 staining was performed. The thickness of the epidermis in the stained sections was measured and compared between MDI 101, all-trans Retinol, all in a concentration of 0.01 µM and the DMSO control (FIG. 1).

| Substance | Thickness (whole) [µm] | Thickness (without stratum corneum) [µm] |
|---|---|---|
| DMSO control (0.1%) | 140 | 90 |
| All-trans Retinol 0.01 µM | 150 | 85 |
| MDI 101 0.01 µM | 157 | 112.5 |

A positive effect of MDI 101 was observed on the thickness of the epidermis, which was better than the effect of all-trans Retinol in the same concentration.

Example 1.6: Solubility and Recrystallization

| Substance | INCI | A1 [wt.-%] | A2 [wt.-%] |
|---|---|---|---|
| MDI 101 | Hydroxypinacolone Retinoate | 2.5 | 2.5 |
| Isoadipate | Diisopropyl Adipate | 96.5 | 97.5 |
| Tocopherol | Tocopherol | 1.0 | — |

Two pre-blends, A1 and A2, both containing 2.5 w/w % of Hydroxypinacolone Retinoate (MDI 101) were produced according to the above recipe. Three o/w emulsions (A, B and C) according to the following recipe were prepared:

| Phase | INCI | A [wt.-%] | B [wt.-%] | C [wt.-%] |
|---|---|---|---|---|
| A | Potassium Cetyl Phosphate, Hydrogenated Palm Glycerides | 2 | 2 | 2 |
|  | Pentaerythrityl Distearate | 1.5 | 1.5 | 1.5 |
|  | Glyceryl Stearate | 2 | 2 | 2 |
|  | Cetearyl Nonanoate | 3 | 3 | 3 |
|  | Caprylic/Capric/Triglceride | 7 | 7 | 7 |
|  | Ethylhexyl Isononanoate | 3 | 3 | 3 |
| B | Acrylates/C10-30 Alkyl Acrylate Crosspolymer | 0.2 | 0.2 | 0.2 |
|  | Xanthan Gum | 0.2 | 0.2 | 0.2 |
| C | Water (Aqua) | 71.90 | 71.90 | 73.85 |
|  | Disodium EDTA | 0.1 | 0.1 | 0.1 |
|  | Pentyleneglycol | 3 | 3 | 3 |
|  | 1,2-Hexanediol, Caprylyl Glycol | 0.6 | 0.6 | 0.6 |
|  | Propylene Glycol | 2 | 2 | 2 |
|  | Glycerin 85% | 1 | 1 | 1 |
| D | Sodium Hydroxide 10% aqueous sol. | 0.5 | 0.5 | 0.5 |
|  | Sum | 98 | 98 | 99.95 |
|  | Pre-blend A1 | 2.0 | — | — |
|  | Pre-blend A2 | — | 2.0 | — |
|  | Only MDI 101 | — | — | 0.05 |
|  | pH value | 5.9 | 5.9 | 5.9 |

Heat Phases A and C separately up to 80° C. Disperse Phase B in A. Add Phase C to AB and emulsify by using an Ultra Turrax Stirrer (3 min, 6000 rpm). Add Phase D and neutralize. Allow to cool by using a vane stirrer.

The emulsions were equal, except for the addition of MDI 101. Whereas in emulsion A and B, 2 wt.-% of the pre-blends as above was incorporated into the o/w emulsion by stirring for 10 minutes at 150 rpm with a vane stirrer and at 35° C., 0.05 wt.-% of MDI 101 itself was incorporated into emulsion C in the same way. As the pre-blends contain 2.5 wt.-% MDI 101, the final concentration of MDI 101 in the emulsions A, B and C was 0.05 wt.-% in all emulsions.

Microscopic images were done of all three emulsions using microscope Olympus IX 70 with polarized light and 60× enlargement (FIG. 3, wherein FIG. 3A shows the results for emulsion A, FIG. 3B shows the results for emulsion B, and FIG. 3C shows the results for emulsion C, respectively).

It could be clearly observed that emulsions A and B (cf. FIG. 3A and FIG. 3B) containing the respective pre-blends showed no crystals whereas emulsion C (cf. FIG. 3C) showed strong recrystallization.

Example 2: Application Examples

Example 2.1: Formulation Example 1: O/W Lotion (Amounts in % b.w.)

| Ingredients | Amount |
| --- | --- |
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerol | 3.00 |
| Perfume oil | 0.30 |
| Methylparaben | 0.30 |
| Retinoic acid, 3,3-dimethyl-2-oxobutyl ester | 0.05 |
| Diisopropyl Adipate | 2.00 |
| 1,2-octandiol | 0.30 |
| Tocopherol | 0.015 |
| Water | ad 100.00 |

Example 2.2: Formulation Example 2: Body Lotion (Amounts in % b.w.)

| Ingredients | Amount |
| --- | --- |
| Cetearyl Alcohol | 2.00 |
| Ethylhexyl Isononanoate | 5.00 |
| Cetearyl Ethylhexanoate. Isopropyl Myristate | 3.00 |
| Glyceryl Oleate Citrate. Caprylic/Capric Triglyceride | 4.00 |
| Water (Aqua) | ad 100 |
| Carbomer | 0.30 |
| Sodium Benzoate | 0.100 |
| Propylene Glycol | 5.00 |
| Sodium Hydroxide 30% solution | 0.30 |
| Perfume oil | 0.30 |
| Triethylene Glycol. Imidazolidinyl Urea. Methylparaben. Propylparaben. Dehydroacetic Acid | 0.30 |
| Retinoic acid, 3,3-dimethyl-2-oxobutyl ester | 0.05 |
| Diisopropyl Adipate | 1.93 |
| Tocopherol | 0.015 |
| 1,2-octandiol | 0.10 |

Example 2.3: Formulation Example 3: Cream (Amounts in % b.w.)

| Ingredients | Amount |
| --- | --- |
| Paraffin oil | 10.00 |
| Ozokerite | 4.00 |
| Vaseline | 4.00 |
| Vegetable oil | 10.00 |
| Wool wax alcohol | 2.00 |
| Aluminium stearate | 0.40 |
| Perfume oil P1. P2. P3 or P4 | 0.70 |
| 1,2-pentanediol | 2.00 |
| Phenoxyethanol | 0.50 |
| Retinoic acid, 3,3-dimethyl-2-oxobutyl ester | 0.025 |
| Diisopropyl Adipate | 0.965 |
| Tocopherol | 0.01 |
| 1,2-octandiol | 0.25 |
| Water | ad 100.00 |

Example 2.4: Formulation Example 4: Cream (Amounts in % b.w.)

| Ingredients | INCI | Amount |
| --- | --- | --- |
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. Cyclosiloxane | Cyclohexasiloxane (and) Cyclopentasiloxane | 0.50 |
| Dragoxat ® 89 | Ethylhexyl Isononanoate | 2.00 |
| PCL-Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan Gum | 0.10 |
| Water | Water (Aqua) | Ad 100 |
| Glycerol 99.5 P. | Glycerol | 3.00 |
| Propylene Glycol -1.2 99 P GC | Propylene Glycol | 2.00 |
| Sodium Benzoate | Sodium Benzoate | 0.10 |
| Sodium Hydroxide 10% solution | Sodium Hydroxide | 0.50 |
| Perfume oil | Perfume | 0.30 |
| Euxyl ® K702 | Dehydroacetic Acid. Benzoic Acid. Phenoxyethanol. Polyaminopropyl Biguanide. Ethylhexylglycerin | 0.30 |
| SymDiol ® 68 | 1,2-hexandiol and 1,2-octandiol | 0.35 |
| Retinoic acid, 3,3-dimethyl-2-oxobutyl ester | | 0.05 |

| Ingredients | INCI | Amount |
|---|---|---|
| Isoadipate | Diisopropyl Adipate | 1.93 |
| Tocopherol | Tocopherol | 0.025 |

Example 2.5: Formulation Example 5: Rescue after Shave (Amounts in % b.w.)

| Phase | Ingredients | INCI | Amount |
|---|---|---|---|
| A | Water | Aqua | Ad 100 |
|  | Carbopol ® Ultrez 21 Polymer | Acrylates/C10-30 Alkyl Acrylate Crosspolymer | 0.60 |
| B | Glycerol | Glycerol | 2.00 |
| C | Biotive ® L-Arginine | Arginine | 0.50 |
| D | Ethanol | Alcohol denat. | 10.00 |
| E | Hydrolite ® 5 | Pentylene Glycol | 5.00 |
|  | Frescolat ® MGA | Menthone Glycerin Acetal | 0.50 |
|  | Xiameter ® PMX-345 | Cyclopentasiloxane, Cyclohexasiloxane | 4.00 |
|  | SymRelief ® 100 | *Zingiber Officinale* Root Extract | 0.10 |
| F | Tapioca Pure | Tapioca Starch | 2.00 |
| G | Fragrance | Parfum | 1.00 |
| H | Retinoic acid, 3,3-dimethyl-2-oxobutyl ester |  | 0.1 |
|  | Isoadipate | Diisopropyl Adipate | 3.86 |
|  | Tocopherol | Tocopherol | 0.03 |

Example 2.6: Formulation Example 6: Rescue after Shave (Amounts in % b.w.)

| Phase | Ingredients | INCI | Amount |
|---|---|---|---|
| A | Water | Aqua | Ad 100 |
|  | Carbopol ® Ultrez 21 Polymer | Acrylates/C10-30 Alkyl Acrylate Crosspolymer | 0.45 |
| B | Sodium Hydroxide 10% Sol. | Sodium Hydroxide | 0.40 |
| C | SymGlucan ® | Aqua, Glycerin, 1,2-Hexanediol, Caprylyl Glycol, Beta-Glucan | 5.00 |
|  | *Aloe Vera* Gel Concentrate | *Aloe Barbadensis* Leaf Juice | 0.50 |
| D | SymOcide ® PH | Phenoxyethanol, Hydroxyacetophenone, Caprylyl Glycol, Aqua | 1.20 |
|  | SymRelief ® 100 | *Zingiber Officinale* Root Extract | 0.10 |
|  | Dracorin ® GOC | Glyceryl Oleate Citrate, Caprylic/Capric Triglyceride | 1.00 |
|  | Frescolat ® ML Cryst. | Menthyl Lactate | 1.00 |
|  | Fragrance | Parfum | 0.30 |
| E | Sodium Hydroxide 30% sol. | Sodium Hydroxide | 0.37 |
| F | Retinoic acid, 3,3-dimethyl-2-oxobutyl ester |  | 0.01 |
|  | Isoadipate | Diisopropyl Adipate | 0.40 |

Example 2.7: Formulation Example 7: Deodorant Roll on (Amounts in % b.w.)

| Phase | Ingredients | INCI | Amount |
|---|---|---|---|
| A | SymSitive ® 1609 | Pentylene Glycol, 4-tButylcyclohexanol | 1.20 |
|  | SymWhite ® 377 | Phenylethyl Resorcinol | 0.30 |
|  | Arlacel 165 | Glyceryl Stearate, PEG-100 Stearate | 3.00 |
|  | Brij ® 72 | Steareth-2 | 0.30 |
|  | Brij ® 721 P | Steareth-21 | 2.50 |
|  | Arlamol PS15 | PPG15 Stearyl Ether | 2.00 |
|  | Lanette ® O OR | Cetearyl Alcohol | 1.00 |
|  | Copherol ® 1250 | Tocopheryl Acetate | 0.50 |
| B | Water | Aqua | Ad 100 |
|  | Glycerin | Glycerin | 2.0 |

| Phase | Ingredients | INCI | Amount |
|---|---|---|---|
| | EDTA NA 2 | Disodium EDTA | 0.10 |
| | SymTriol ® | Caprylyl Glycol, 1,2-Hexanediol, Methylbenzyl Alcohol | 0.60 |
| | Veegum HV | Magnesium Aluminium Silicate | 1.00 CC |
| C | Water | Aqua | 3.00 |
| | Covastyle MBS | Sodium Metabisulfite | 0.15 |
| D | Oxynex ST liquid | Diethylhexyl Syringylidemalonate, Caprylic Capric Triglycerides | 0.10 |
| | SymDeo ® B125 | 2-Methyl-5-cyclohexylpentanol | 0.50 |
| E | Extrapone ® Aquamarine GW | Aqua, Glycerin, Xanthan Gum, Aquamarine Powder | 0.50 |
| G | Fragrance | Parfum | 1.00 |
| H | Retinoic acid, 3,3-dimethyl-2-oxobutyl ester | | 0.025 |
| | Isoadipate | Diisopropyl Adipate | 2.00 |

Example 2.8: Formulation Example 8: After Shave Gel (Amounts in % b.w.)

| Phase | Ingredients | INCI | Amount |
|---|---|---|---|
| A | SymSol ® PF-3 | Aqua, Pentylene Glycol, Sodium Lauryl Sulfoacetate, Sodium Oleyl Sarcosinate, Sodium Chloride, Disodium Sulfoacetate, Sodium Oleate, Sodium Sulfate | 3.00 |
| | SymSitive ® 1609 | Pentylene Glycol, 4-tButylcyclohexanol | 1.00 |
| | Frescolat ® ML | Menthyl Lactate | 0.30 |
| | Fragrance | Parfum | 0.15 |
| | Glycerin | Glycerin | 5.00 |
| B | Water | Aqua | Ad 100 |
| | Pemulen ® TR-2 Polymeric Emulsifier | Acrylates/C10-30 Alkyl Acrylate Crosspolymer | 1.00 |
| | Extrapone ® Glacier Water GW | Glycerin, Aqua | 1.00 |
| | SymCalmin ® | Pentylene Glycol, Butylene Glycol, Hydroxyphenylpropamidobenzoic Acid | 0.50 |
| | Dragosine ® | Carnosin | 0.10 |
| | Hydrolite ® 5 | Pentylene Glycol | 5.00 |
| | Sodium Hydroxide 10% Sol. | Sodium Hydroxide | 3.15 |
| C | Ethanol | Alcohol denat. | 10.00 |
| | Colour | Colour | 0.50 |
| D | Retinoic acid, 3,3-dimethyl-2-oxobutyl ester | | 0.025 |
| | Isoadipate | Diisopropyl Adipate | 2.00 |

Example 2.9: Formulation Example 9: Deo Stick (Amounts in % b.w.)

| Phase | Ingredients | INCI | Amount |
|---|---|---|---|
| A | Dragoxat ® 89 | Ethylhexyl Isononanoate | 1.00 |
| | 1,2 Propylene Glycol | Propylene Glycol | 54.50 |
| | Sodium Stearate | Sodium Stearate | 8.00 |
| | Hydrolite ® 5 | Pentylene Glycol | 0.50 |
| | Retinoic acid, 3,3-dimethyl-2-oxobutyl ester | | 0.040 |
| | Isoadipate | Diisopropyl Adipate | 0.50 |
| | Glycerin | Glycerine | 20.00 |
| | Water | Aqua | Ad 100 |
| B | SymDeo ® B 125 | 2-Methyl 5-Cyclohexylpentanol | 0.50 |
| | Fragrance | Parfüm | 1.50 |

Example 2.10: Formulation Example 10: Hand and Body Cream (Amounts in % b.w.)

| Ingredients | INCI | Amount |
|---|---|---|
| Dracorin ® GOC | Glyceryl Oleate Citrate. Caprylic/Capric Triglyceride | 2.00 |
| PCL-Solid | Stearyl Heptanoate. Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL-Liquid 100 | Cetearyl Ethylhexanoate | 7.00 |
| Isodragol ® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan Gum | 0.10 |
| Glycerol 85 P. | Glycerol | 3.00 |
| DragoBetaGlucan | Water (Aqua). Butylene Glycol. Glycerol. *Avena Sativa* (Oat) Kernel Extract | 1.50 |
| Potassium Sorbat | Potassium Sorbate | 0.10 |
| Sodium Hydroxide 10% solution | Sodium Hydroxide | 0.50 |
| Perfume oil | Parfum | 0.20 |
| Euxyl ® K300 | Methyl-. Butyl-. Ethyl-. Propyl. Isobutylparaben. Phenoxyethanol. | 0.30 |
| Retinoic acid, 3,3-dimethyl-2-oxobutyl ester | | 0.005 |
| Isoadipate | Diisopropyl Adipate | 1.00 |
| SymDiol ® 68 | 1,2-hexandiol and 1,2-octandiol | 0.10 |

Example 2.11: Formulation Example 11: Face Cream (Amounts in % b.w.)

| Ingredients | INCI | Amount |
|---|---|---|
| Emulsiphos ® | Potassium Cetyl Phosphate. Hydrogenated Palm Glycerides | 1.50 |
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL-Liquid 100 | Cetearyl Ethylhexanoate | 1.00 |
| Isodragol ® | Triisononanoin | 3.00 |
| Dragoxat ® 89 | Ethylhexyl Isononanoate | 4.00 |
| Avocado Oil | *Persea Gratissima* (Avocado) Oil | 3.00 |
| Abil ® 350 | Dimethicone | 0.50 |
| Covi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan Gum | 0.150 |
| Water | Water (Aqua) | Ad 100 |
| Glycerol 99.5 P. | Glycerol | 4.00 |
| Propylene Glycol -1.2 99 P GC | Propylene Glycol | 3.00 |
| SymMatrix ® | Maltodextrin. *Rubus Fruticosus* (Blackberry) Leaf Extract | 0.50 |
| Sodium Hydroxide 10% solution | Sodium Hydroxide | 0.50 |
| Perfume oil | Parfum | 0.30 |
| Euxyl ® K712 | Sodium Benzoate. Potassium Sorbate | 0.20 |
| Retinoic acid, 3,3-dimethyl-2-oxobutyl ester | | 0.075 |
| Isoadipate | Diisopropyl Adipate | 1.50 |
| SymDiol ® 68 | 1,2-hexandiol and 1,2-octandiol | 0.35 |

Example 2.12: Formulation Example 12: Moisturizing Body Care Cream (Amounts in % b.w.)

| Ingredient | Amount |
| --- | --- |
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (*Butyrospermum parkii*) | 0.50 |
| Aluminum stearate | 0.50 |
| Magnesium stearate | 0.50 |
| Bisabolol | 0.20 |
| Quaternium-18-Hectorit | 0.70 |
| Dipropylene glycol | 5.0 |
| Magnesium sulfate | 0.70 |
| Pentylene glycol | 4.00 |
| Perfume oil | 0.30 |
| Preservative (Phenoxyethanol) | 0.20 |
| Capsaicin | 0.20 |
| 1,2-Heptandiol | 0.20 |
| Retinoic acid, 3,3-dimethyl-2-oxobutyl ester | 0.05 |
| Diisopropyl Adipate | 2.00 |
| Aqua dem. | Ad 100 |

Example 2.13: Formulation Example 13: Anti-Wrinkle Cream (Amounts in % b.w.)

| Ingredients | Amount |
| --- | --- |
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclopentasiloxane, Cyclohexasiloxane | 0.50 |
| Acrylates/C10-30 Alkyl Acrylate Crosspolymer | 0.20 |
| Water | Ad 100 |
| 1.2-Hexanediol | 2.00 |
| Sodium Hydroxide 10% solution | 0.10 |
| *Narcissus Tazetta* Bulb Extract | 1.00 |
| Perfume oil | 0.30 |
| Preservative (Phenoxyethanol) | 0.50 |
| Retinoic acid, 3,3-dimethyl-2-oxobutyl ester | 0.025 |
| Diisopropyl Adipate | 1.00 |
| 1,2-Heptandiol | 0.25 |

Example 2.14: Formulation Example 14: Septic Wound Cream (Amounts in % b.w.)

| Ingredients (INCI) | Amount |
| --- | --- |
| Sorbitan Isostearate. Hydrogenated Castor Oil. Ceresin. Beeswax (Cera Alba) | 6.00 |
| Petrolatum | 21.00 |
| Cera Alba | 5.00 |
| Cetearyl Alcohol | 7.00 |
| *Prunus Dulcis* | 7.00 |
| Lanolin | 5.00 |
| Paraffinum Liquidum | 12.00 |
| Perfume oil P1. P2. P3 or P4 | 0.30 |
| Water (Aqua) | Ad 100 |
| Panthenol | 7.00 |
| Magnesium Sulfate | 0.70 |
| Pentylene Glycol | 1.00 |
| Tocopheryl Acetate | 1.00 |
| Octenidine dihydrochloride | 0.10 |
| Phenoxyethanol | 0.50 |
| Retinoic acid, 3,3-dimethyl-2-oxobutyl ester | 0.005 |
| Diisopropyl Adipate | 0.10 |
| 1,2-octandiol | 0.25 |

Example 2.15: Formulation Example 15: Moisturizing and Disinfecting Face Mask (Amounts in % b.w.)

| Ingredients | INCI | Amount |
| --- | --- | --- |
| Water | Water (Aqua) | Ad 100 |
| Stabileze QM | PVM/Ma Decadiene Crosspolymer | 0.50 |
| Biotive ® L-Arginine | Arginine | 0.75 |
| Actipone ® *Laminaria Saccharina* GW | Glycerol. Water (Aqua). *Laminaria Saccharina* Extract | 1.00 |
| Extrapone ® Cucumber | Water (Aqua). Propylene Glycol. *Cucumis Sativus* (Cucumber) Juice | 1.00 |
| Glycerol 99.5 P. | Glycerol | 7.00 |
| Neo Actipone ® Soap Nutshell | *Sapindus Mukurossi* Peel Extract | 0.50 |
| Colour I | Colour | 0.01 |
| Hydrolite ® 5 | Pentylene Glycol | 5.00 |
| Solubilizer | PEG-40 Hydrogenated Castor Oil. Trideceth-9. Water (Aqua) | 0.60 |
| Perfume oil | Parfum | 0.08 |
| Preservative | Phenoxyethanol | 0.40 |
| Retinoic acid, 3,3-dimethyl-2-oxobutyl ester | | 0.05 |
| Isoadipate | Diisopropyl Adipate | 1.93 |
| SymDiol ® 68 | 1,2-hexandiol and 1,2-octandiol | 0.20 |

Example 2.16: Formulation Example 16: Anti-Acne Wash (Amounts in % b.w.)

| Ingredients (INCI) | Amount |
| --- | --- |
| Water (Aqua) | 45.70 |
| Polyquaternium-7 | 0.50 |
| Cocamidopropyl Betaine 9.000 | 9.00 |
| Coco Glucoside 2.000 | 2.00 |
| Polysorbate 80. Glycerol. *Gossypium Herbaceum*. (Cotton) Seed Oil. Water (Aqua) | 1.00 |
| Trideceth-9. PEG-5 Ethylhexanoate. Water (Aqua) | 1.00 |
| Glycereth-90 Isostearate. Laureth-2 | 0.50 |
| Sodium Laureth Sulfate 37.000 | 37.00 |
| Glycerol. *Triticum Vulgare* (Wheat) Gluten. Water (Aqua) | 1.00 |
| Sodium Chloride | 0.30 |
| Perfume oil | 1.00 |
| Phenoxyethanol, Methylparaben, Ethylparaben, Butylparaben, Propylparaben, Isobutylparaben | 0.30 |
| Retinoic acid, 3,3-dimethyl-2-oxobutyl ester | 0.1 |
| Diisopropyl Adipate | 5.00 |
| 1,2-octandiol | 0.25 |

Example 2.17: Formulation Example 17: Cosmetic Sun Protection Composition (Amounts in % b.w.)

| Ingredient | Amount |
| --- | --- |
| Ethylhexyl cinnamic acid | 7.50 |
| Benzophenon-3 | 2.00 |
| Polyglyceryl dimer soyate | 0.80 |
| Sorbitane stearate | 1.00 |
| Tocopheryl acetate | 0.50 |
| Glyceryl stearate. PEG-100 Stearate | 3.00 |
| PEG-40. hydrogenated castor oil | 1.00 |
| Titanium dioxide. aluminum oxide hydrate. Dimethicon/Methicon Copolymer | 3.00 |
| *Butyrospermum parkii* (Shea Butter) | 1.00 |
| $C_{12-15}$ alkyl benzoate | 6.50 |
| Butylene glycol | 5.00 |
| Xanthan gum | 0.30 |
| Disodium EDTA | 0.10 |
| Allantoin | 0.10 |
| Polyacryl amide. $C_{13-14}$ isoparaffin. Laureth-7 | 1.00 |
| Pentylene glycol | 5.00 |
| 4-t Butylcyclohexanol | 1.00 |
| Perfume oil | 0.30 |
| Preservatives (Methyl-. Butyl-. Ethyl-. Propylparaben. Phenoxyethanol) | 0.30 |
| Retinoic acid, 3,3-dimethyl-2-oxobutyl ester | 0.03 |
| Diisopropyl Adipate | 0.10 |
| 1,2-Heptandiol | 0.25 |
| Aqua dem. | Ad 100 |

Example 2.18: Formulation Example 18: Sun Protection Spray (Amounts in % b.w.)

| Ingredients | INCI | Amount |
| --- | --- | --- |
| Water. demineralized | Water (aqua) | 69.50 |
| Glycerol | Glycerol | 4.00 |
| 1.3 butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH. 10% | Sodium hydroxide | 0.60 |
| Perfume oil P1. P2. P3 or P4 | Fragrance | 0.20 |
| Phenoxyethanol | Phenoxyethanol | 0.40 |
| Solbrol M | Methylparaben | 0.10 |
| Solbrol P | Propylparaben | 0.10 |
| Retinoic acid, 3,3-dimethyl-2-oxobutyl ester | | 0.05 |
| Isoadipate | Diisopropyl Adipate | 0.40 |
| Hydrolite 5 | 1,2-Heptandiol | 0.25 |

Example 2.19: Formulation Example 19: Sunscreen Spray O/W. SPE15-20 (Amounts in % b.w.)

| Ingredients | INCI | Amount |
|---|---|---|
| Dracorin ® GOC | Glyceryl Oleate Citrate. Caprylic/Capric Triglyceride | 2.00 |
| Corapan ® TQ | Diethylhexyl 2.6-Naphthalate | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl Adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Aerylates/C10-30 Alkyl Acrylate Crosspolymer | 0.25 |
| Water | Water (Aqua) | Ad 100 |
| Glycerol 99.5 P. | Glycerol | 4.00 |
| Butylene Glycol | Butylene Glycol | 5.00 |
| Neo Heliopan ® Hydro (103089). used as 25% aq. solution neutralized with Biotive ® L-Arginine | Phenylbenzimidazole Sulfonic Acid | 8.00 |
| Biotive ® L-Arginine | Arginine | 0.55 |
| Perfume oil | Fragrance | 0.40 |
| Sobrol M | Methylparaben | 0.30 |
| Retinoic acid, 3,3-dimethyl-2-oxobutyl ester | | 0.001 |
| SymDiol ® 68 | 1,2-hexandiol and 1,2-octandiol | |

Example 2.20: Formulation Example 20: Sun Protection Soft Cream (W/O). SPF 40 (Amounts in % b.w.)

| Ingredients | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 Alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide. neutral | Zinc oxide | 5.00 |
| Water. distilled | Water (aqua) | Add 100 |
| EDETA BD | Disodium EDTA | 0.10 |
| Glycerol | Glycerol | 4.00 |
| Magnesium sulfate | Magnesium sulfate | 0.50 |
| Perfume oil | Parfum | 0.30 |
| SymDiol ® 68 | 1,2 hexandiol (and) 1,2 octandiol | 0.30 |
| Retinoic acid, 3,3-dimethyl-2-oxobutyl ester | | 0.001 |
| Isoadipate | Diisopropyl Adipate | 6.00 |

Example 2.21: Formulation Example 21: Sun Protection Milk (W/O) (Amounts in % b.w.)

| Ingredients | INCI | Amount |
|---|---|---|
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |

-continued

| Ingredients | INCI | Amount |
|---|---|---|
| Uvinul ® T150 | Ethylhexyl triazone | 1.50 |
| Water. distilled | Water (Aqua) | To 100 |
| Trilon BD | Disodium EDTA | 0.10 |
| Glycerol | Glycerol | 5.00 |
| Neo Heliopan ® AP 10% solution. neutralized with NaOH | Disodium phenyl dibenzimidazole tetrasulfonate | 15.00 |
| Perfume oil | Parfum | 0.25 |
| Alpha bisabolol | Bisabolol | 0.10 |
| SymOcide ® PT | Phenoxyethanol. Tropolone | 0.25 |
| SymDiol ® 68 | 1,2 hexandiol (and) 1,2 octandiol | 0.10 |
| Retinoic acid, 3,3-dimethyl-2-oxobutyl ester, dissolved in diisopropyl adipate (## %) | | 0.0015 |
| Isoadipate | Diisopropyl Adipate | 9.00 |

Example 2.22: Formulation Example 22: After Sun Gel (Amounts in % b.w.) Ingredients INCI Amount

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.000 |
| Glycerol 99.5 P. | Glycerol | 5.000 |
| SymHelios ® 1031 | Benzylidene Dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |
| D-Panthenol 75 W | Panthenol | 0.500 |
| SymFinity ® 1298 | *Echinacea Purpurea* Extract | 0.100 |
| Extrapone ® Pearl GW | Water (Aqua). Glycerol. Hydrolyzed Pearl. Xanthan Gum | 1.000 |
| Sodium Hydroxide 10% solution | Sodium Hydroxide | 2.500 |
| Ethanol 96% | Alcohol Denat. | 15.000 |
| Perfume oil | Parfum | 0.20 |
| SymOcide ® PS | Phenoxyethanol. 1.2-Hexanediol. Decyleneglycol | 0.50 |
| SymDiol ® 68 | 1,2 hexandiol (and) 1,2 octandiol | 0.25 |
| Retinoic acid, 3,3-dimethyl-2-oxobutyl ester | | 0.0025 |
| Isoadipate | Diisopropyl Adipate | 15.00 |

Example 2.23: Formulation Example 23: After Sun Lotion (Amounts in % b.w.)

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil | 0.30 |
| 1.2-Hexanediol | 0.20 |
| Retinoic acid, 3,3-dimethyl-2-oxobutyl ester | 0.01 |
| Diisopropyl Adipate | 1.00 |
| Pentylene glycol | 4.0 |
| Aqua dem. | Ad 100 |
| Triethanolamine | 0.2 |

Example 2.24: Formulation Example 24: Silicone Emulsion (Amounts in % b.w.)

| Ingredients | Amount |
|---|---|
| Potassium Cetyl Phosphate. Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate. Stearyl Caprylate | 3.00 |
| Dimethicone | 1.00 |
| Xanthan Gum | 0.20 |
| Isoamyl p-Methoxycinnamate | 5.00 |
| Water | Ad 100 |
| Methylpropanediol | 3.00 |
| Perfume oil | 0.30 |
| 1.2-Hexanediol | 0.25 |
| Retinoic acid, 3,3-dimethyl-2-oxobutyl ester | 0.01 |
| Diisopropyl Adipate | 0.50 |

Example 2.25: Formulation Example 25:
Microemulsion Gel (Amounts in % b.w.)

| Ingredient | Amount |
|---|---|
| Glycerol isostearate | 1.80 |
| Octoxyglycerol | 1.00 |
| Ceteareth-15 | 5.20 |
| PEG-150 Distearate | 1.00 |
| Aluminium chlorohydrate | 5.00 |
| Isotridecylisononanoate | 3.30 |
| Cyclomethicone | 6.60 |
| Perfume oil | 0.70 |
| 1.2-Hexanediol | 0.20 |
| Retinoic acid, 3,3-dimethyl-2-oxobutyl ester | 0.002 |
| Diisopropyl Adipate | 5.00 |
| Water | Ad 100 |

The invention claimed is:
1. A mixture comprising:
(a) 0.5 to 10 wt.-% of one or more compound(s) of formula 1, and

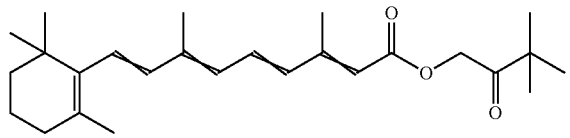

(formula 1)

(b) diisopropyl adipate;
wherein the one or more compound(s) of formula 1 is not crystallized in the mixture.
2. The mixture of claim 1, further comprising tocopherol.
3. The mixture of claim 2 comprising:
(a) 0.5 to 10 wt.-% of the compound of formula 1;
(b) diisopropyl adipate; and
(c) 0.1 to 5 wt.-% tocopherol.
4. The mixture of claim 1 consisting of:
(a) 0.5 to 10 wt.-% of the compound of formula 1;
(b) diisopropyl adipate; and
(c) optionally, 0.1 to 5 wt.-% tocopherol.
5. A cosmetic or pharmaceutical composition comprising:
(a) the mixture of claim 1 in an amount such that the total amount of the one or more compound(s) of formula 1 in the composition is from 0.0001 to 1 wt.-%, based on the total weight of the composition; and
(b) a cosmetically or pharmaceutically acceptable carrier;
wherein the one or more compound(s) of formula 1 is not crystallized in the composition.
6. The cosmetic or pharmaceutical composition of claim 5, wherein the total amount of the one or more compound(s) of formula 1 in the composition is from 0.001 to 0.1 wt.-%, based on the total weight of the composition.
7. The cosmetic or pharmaceutical composition of claim 5, wherein the cosmetically or pharmaceutically acceptable carrier is chosen from one or more glycols, aliphatic esters, alkyl alcohols, alkenyl alcohols, branched and unbranched hydrocarbons and waxes, cyclic and linear silicone oils, and dialkyl ethers having 6 to 24 carbon atoms.
8. A cosmetic or pharmaceutical composition comprising:
(a) the mixture of claim 1 in an amount such that the total amount of the one or more compound(s) of formula 1 in the composition is from 0.001 to 0.1 wt.-%, based on the total weight of the composition;
(b) a cosmetically or pharmaceutically acceptable carrier chosen from one or more glycols, aliphatic esters, alkyl alcohols, alkenyl alcohols, branched and unbranched hydrocarbons and waxes, cyclic and linear silicone oils, and dialkyl ethers having 6 to 24 carbon atoms; and
(c) 40 to 90 wt. % of water, based on the total weight of the composition;
wherein the one or more compound(s) of formula 1 is not crystallized in the composition.
9. The cosmetic or pharmaceutical composition of claim 8 in the form of an emulsion.
10. The cosmetic or pharmaceutical composition of claim 5, further comprising one or more substances chosen from:
(i) anti-itch compounds,
(ii) steroidal anti-inflammatory substances of the corticosteroid type,
(iii) non-steroidal anti-inflammatory substances,
(iv) natural or naturally occurring anti-inflammatory substances,
(v) alpha-bisabolol, apigenin, apigenin-7-glucoside, gingerols, shogaols, gingerdiols, dehydrogingerdiones, paradols, natural avenanthramides, non-natural avenanthramides,
(vi) skin care agents chosen from sodium lactate, urea and derivatives, glycerol, propylene glycol, 1,2-pentanediol, 1,2-hexanediol and 1,2-octanediol, collagen, elastin or hyaluronic acid, diacyl adipates, petrolatum, urocanic acid, lecithin, allantoin, panthenol, phytantriol, lycopene, (pseudo-) ceramides, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide), glycosphingolipids, cholesterol, phytosterols, chitosan, chondroitin sulfate, lanolin, lanolin esters, amino acids, vitamin E and derivatives, alpha-hydroxy acids and derivatives thereof, mono-, di- and oligosaccharides,
(vii) physiological cooling agents, and
(viii) histamine receptor antagonists, serine protease inhibitors, TRPV1 antagonists, NK1 antagonists, cannabinoid receptor agonists and TRPV3 antagonists.
11. A method for improving the complexation of human skin comprising topically applying the composition of claim 5 to the skin.
12. The method of claim 11, wherein the composition is applied to skin and remains on the skin for at least 5 minutes.
13. The method of claim 11, wherein the mixture is applied to skin and remains on the skin for at least 10 minutes.
14. The mixture of claim 1, wherein the mixture is free from ethanol and isopropyl alcohol.
15. The composition of claim 8, wherein the compositions is free from ethanol and isopropyl alcohol.

* * * * *